(12) United States Patent
Juhl et al.

(10) Patent No.: US 11,827,665 B2
(45) Date of Patent: *Nov. 28, 2023

(54) PROCESS FOR THE MANUFACTURE OF (2S,3S,4S,5R,6S)-3,4,5-TRIHYDROXY-6-(((4AR,10AR)-7-HYDROXY-1-PROPYL-1,2,3,4,4A,5,10,10A-OCTAHYDROBENZO[G]QUINOLIN-6-YL)OXY)TETRAHYDRO-2H-PYRAN-2-CARBOXYLIC ACID

(71) Applicant: H. Lundbeck A/S, Valby (DK)

(72) Inventors: Martin Juhl, Valby (DK); Lisbet Kværnø, Valby (DK); Mikkel Fog Jacobsen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/385,166

(22) Filed: Jul. 26, 2021

(65) Prior Publication Data

US 2022/0185839 A1 Jun. 16, 2022

Related U.S. Application Data

(63) Continuation of application No. 16/876,843, filed on May 18, 2020, now Pat. No. 11,104,697.

(30) Foreign Application Priority Data

May 20, 2019 (DK) .............. PA201900598

(51) Int. Cl.
C07H 15/26 (2006.01)
(52) U.S. Cl.
CPC ................... C07H 15/26 (2013.01)
(58) Field of Classification Search
None
See application file for complete search history.

(56) References Cited

U.S. PATENT DOCUMENTS

| | | |
|---|---|---|
| 3,132,171 A | 5/1964 | Plaut |
| 4,543,256 A | 9/1985 | Neumeyer |
| 4,565,818 A | 1/1986 | Nordmann et al. |
| 4,692,453 A | 9/1987 | Seiler |
| 5,073,547 A | 12/1991 | Casagrande et al. |
| 5,747,513 A | 5/1998 | Montanari et al. |
| 5,885,988 A | 3/1999 | Neumann et al. |
| 5,955,468 A | 9/1999 | Markstein |
| 8,129,530 B2 | 3/2012 | Jorgensen et al. |
| 10,729,710 B2 | 8/2020 | Jensen et al. |
| 11,104,697 B2 * | 8/2021 | Juhl ............ C07H 15/26 |
| 11,110,110 B2 | 9/2021 | Jensen et al. |
| 11,111,263 B2 | 9/2021 | Juhl et al. |
| 11,130,775 B2 | 9/2021 | Jensen et al. |
| 11,168,056 B2 | 11/2021 | Jacobsen et al. |
| 11,707,476 B2 | 7/2023 | Jensen et al. |
| 2009/0062324 A1 | 3/2009 | Jorgensen et al. |
| 2009/0124651 A1 | 5/2009 | Jorgensen et al. |
| 2012/0077836 A1 | 3/2012 | Wilkstrom et al. |
| 2017/0335357 A1 | 11/2017 | Divi et al. |
| 2020/0338102 A1 | 1/2020 | Balmer et al. |
| 2020/0369615 A1 | 11/2020 | Jacobsen et al. |
| 2020/0369705 A1 | 11/2020 | Juhl et al. |
| 2020/0369706 A1 | 11/2020 | Juhl et al. |
| 2020/0392176 A1 | 12/2020 | Jensen et al. |
| 2022/0024875 A1 | 1/2022 | Jacobsen et al. |
| 2022/0024962 A1 | 1/2022 | Jensen et al. |
| 2022/0194978 A1 | 6/2022 | Juhl et al. |
| 2022/0213040 A1 | 7/2022 | Jorgensen et al. |
| 2022/0213071 A1 | 7/2022 | Jorgensen et al. |
| 2022/0213136 A1 | 7/2022 | Jorgensen et al. |
| 2022/0220077 A1 | 7/2022 | Jorgensen et al. |
| 2022/0257623 A1 | 8/2022 | Jensen et al. |

FOREIGN PATENT DOCUMENTS

| | | |
|---|---|---|
| CN | 102746351 A | 10/2012 |
| CN | 105218606 A | 1/2016 |
| EP | 0 352 815 A1 | 1/1990 |
| GB | 2 192 394 A | 1/1998 |
| JP | S60-172975 A | 9/1985 |
| JP | 2010-536889 A | 12/2010 |

(Continued)

OTHER PUBLICATIONS

International Search Report and Written Opinion for Application No. PCT/EP2020/063915 dated Jul. 13, 2020.

(Continued)

*Primary Examiner* — Traviss C McIntosh, III

(74) *Attorney, Agent, or Firm* — Wolf, Greenfield & Sacks, P.C.

(57) ABSTRACT

The present invention relates to a process for manufacturing (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below and pharmaceutically acceptable salts thereof

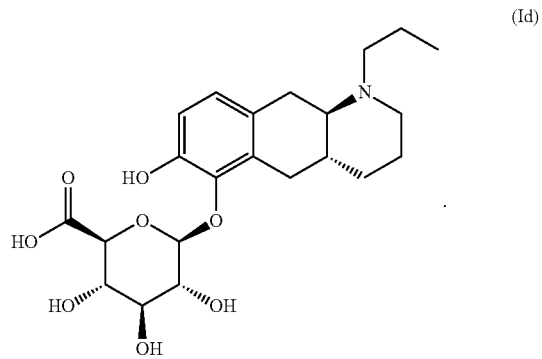

(Id)

The compound of formula (Id) is a prodrug of a catecholamine for use in treatment of neurodegenerative diseases and disorders such as Parkinson's Disease.
The invention also relates to a new intermediate of said process.

21 Claims, 7 Drawing Sheets

(56) References Cited

FOREIGN PATENT DOCUMENTS

| WO | WO 90/12574 A1 | 11/1990 |
|---|---|---|
| WO | WO 97/03054 A1 | 1/1997 |
| WO | WO 98/38155 A1 | 9/1998 |
| WO | WO 00/47571 A1 | 8/2000 |
| WO | WO 01/36428 A1 | 5/2001 |
| WO | WO 01/76602 A1 | 10/2001 |
| WO | WO 01/78713 A1 | 10/2001 |
| WO | WO 02/13827 A1 | 2/2002 |
| WO | WO 02/100377 A1 | 12/2002 |
| WO | WO 03/006458 A1 | 1/2003 |
| WO | WO 03/013532 A1 | 2/2003 |
| WO | WO 03/074511 A1 | 9/2003 |
| WO | WO 03/080074 A1 | 10/2003 |
| WO | WO 2004/052841 A1 | 6/2004 |
| WO | WO 2005/062894 A2 | 7/2005 |
| WO | WO 2006/012640 A2 | 2/2006 |
| WO | WO 2006/056604 A1 | 6/2006 |
| WO | WO 2009/026934 A1 | 3/2009 |
| WO | WO 2009/026935 A1 | 3/2009 |
| WO | WO 2010/097091 A1 | 9/2010 |
| WO | WO 2010/097092 A1 | 9/2010 |
| WO | WO 2013/020979 A1 | 2/2013 |
| WO | WO 2013/034119 A1 | 3/2013 |
| WO | WO 2015/067927 A1 | 5/2015 |
| WO | WO 2016/065019 A1 | 4/2016 |
| WO | WO 2017/184871 A1 | 10/2017 |
| WO | WO 2019/101917 A1 | 5/2019 |

OTHER PUBLICATIONS

International Search Report and Written Opinion for Application No. PCT/EP2020/063916 dated Sep. 28, 2020.

International Search Report and Written Opinion for Application No. PCT/EP2020/063918 dated Aug. 10, 2020.

International Search Report and Written Opinion for Application No. PCT/EP2020/063914 dated Jul. 14, 2020.

International Search Report and Written Opinion for Application No. PCT/EP2018/082361 dated Feb. 22, 2019.

International Search Report and Written Opinion for Application No. PCT/EP2020/063909 dated Jul. 2, 2020.

International Search Report and Written Opinion for Application No. PCT/EP2020/063910 dated Jul. 14, 2020.

International Search Report and Written Opinion for Application No. PCT/EP2020/063913 dated Jul. 15, 2020.

International Search Report and Written Opinion for Application No. PCT/EP2020/063908 dated Sep. 11, 2020.

Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/ol800722a. Epub May 14, 2008.

Alexander et al., Functional architecture of basal ganglia circuits: neural substrates of parallel processing. Trends Neurosci. Jul. 1990;13(7):266-71.

Atkinson et al., Derivatives of apomorphine and of other N-substituted norapomorphines. J Pharm Sci. Nov. 1976;65(11):1682-5.

Bibbiani et al., Continuous dopaminergic stimulation reduces risk of motor complications in parkinsonian primates. Exp Neurol. Mar. 2005;192(1):73-8.

Billeter et al., 8-Hydroxyflavonoid Glucuronides from Malva Sylvestris. Phytochemistry. 1991;30(3):987-90.

Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.

Campbell et al., Behavioral effects of (−)10,11-methylenedioxy-N-n-propylnoraporphine, an orally effective long-acting agent active at central dopamine receptors, and analogous aporphines. Neuropharmacology. Oct. 1982;21(10):953-61.

Cannon et al., N-Alkyl derivatives of trans-6,7-dihydroxy-1,2,3,4,4a,5,10,10b-octahyrobenzo[g]quinoline A congener of apomorphine lacking the non-oxygenated aromatic ring. J. Heterocyclic Chem. Nov. 1980;17:1633-1636.

Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.

Delong, Primate models of movement disorders of basal ganglia origin. Trends Neurosci. Jul. 1990;13(7):281-5.

Di Stefano et al., Antiparkinson prodrugs. Molecules. Jan. 16, 2008;13(1):46-68.

Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.

Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008. (citation on PubMed).

Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.

Gerfen et al., D1 and D2 dopamine receptor-regulated gene expression of striatonigral and striatopallidal neurons. Science. Dec. 7, 1990;250(4986):1429-32.

Giardina et al., Adrogolide HCI (ABT-431; DAS-431), a prodrug of the dopamine D1 receptor agonist, A-86929: preclinical pharmacology and clinical data. CNS Drug Rev. 2001 Fall;7(3):305-16.

Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9.

Grosset et al., Inhaled dry powder apomorphine (VR040) for 'off' periods in Parkinson's disease: an in-clinic double-blind dose ranging study. Acta Neurol Scand. Sep. 2013; 128(3):166-71. doi: 10.1111/ane.12107. Epub Mar. 26, 2013.

Hauser et al., Sublingual apomorphine (APL-130277) for the acute conversion of OFF to ON in Parkinson's disease. Mov Disord. Sep. 2016;31(9):1366-72. Epub Jul. 19, 2016.

Knobloch et al., Keto Esters Derived from 2-(Trimethylsilyl) ethanol: An Orthogonal Protective Group for β-Keto Esters. Synthesis 2008.14 (2008): 2229-2246.

Kotsuki et al., Highly practical, enantiospecific synthesis of the cyclohexyl fragment of the immunosuppressant FK-506. J Org Chem. Aug. 1992;57(18):5036-40.

Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.

Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4): 1494-8. Erratum in: J Med Chem. Nov. 16, 2006;49(23):6930.

Loozen et al., An approach to the synthesis of [2] benzopyrano [3, 4?c] pyrroles; alternative dopaminergic molecules. Recueil des Travaux Chimiques des Pays?Bas. 1982;101(9):298-310.

Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.

Nolen et al., Budesonide-beta-D-glucuronide: a potential prodrug for treatment of ulcerative colitis. J Pharm Sci. Jun. 1995;84(6):677-81.

Poewe et al., Parkinson disease. Nat Rev Dis Primers. Mar. 23, 2017;3:17013.

Rothman et al., Evidence for possible involvement of 5-HT(2B) receptors in the cardiac valvulopathy associated with fenfluramine and other serotonergic medications. Circulation. Dec. 5, 2005;102(23):2836-41.

(56) References Cited

OTHER PUBLICATIONS

Sozio et al., Designing prodrugs for the treatment of Parkinson's disease. Expert Opin Drug Discov. May 2012;7(5):385-406. Epub Apr. 12, 2012.

Sprenger et al., Management of motor and non-motor symptoms in Parkinson's disease. CNS Drugs. Apr. 2013;27(4):259-72.

Stain-Texier et al., Intestinal absorption and stability of morphine 6-glucuronide in different physiological compartments of the rat. Drug Metab Dispos. May 1998;26(5):383-7.

Zhang et al., Flavonoid metabolism: the synthesis of phenolic glucuronides and sulfates as candidate metabolites for bioactivity studies of dietary flavonoids. Tetrahedron. 2012; 68:4194-4201.

U.S. Appl. No. 16/197,917, filed Nov. 23, 2018, Granted, U.S. Pat. No. 10,729,710.

U.S. Appl. No. 17/386,686, filed Jul. 28, 2021, Allowed, 2022-0257623.

U.S. Appl. No. 17/391,439, filed Aug. 2, 2021, Published, 2022-0194978.

U.S. Appl. No. 17/392,970, filed Aug. 3, 2021, Published, 2022-0024962.

U.S. Appl. No. 17/495,997, filed Oct. 7, 2021, Published, 2022-00248752.

Banker et al., Modern Pharmaceuticals. Third Edition, Revised and Expanded. Marcel Dekker, Inc., New York, 1996. p. 596.

David et al., Control of catalytic debenzylation and dehalogenation reactions during liquid-phase reduction by $H_2$. Journal of Catalysis. 2006; 237(2): 349-358.

Kummerer, K. Pharmaceuticals in the Environment. Annu. Rev. Environ. Resour. 2010. 35:57-75. doi: 10.1146/annurev-environ-052809-161223.

Levin et al., Cognitive and neuropsychiatric disorders in extrapyramidal diseases. Neurology, Neuropsychiatry, Psychosomatics. 2012;4(2S):22-30. https://doi.org/10.14412/2074-2711-2012-2505.

Mironov, The Guidelines for Preclinical Trials of Medicinal Products. Grif & Co. Moscow, Russia. 2012. 941 pages.

Przedborski et al., Neurodegeneration: What is it and where are we? J Clin Invest. 2003;111(1):3-10. https://doi.org/10.1172/JCI17522.

Sun et al., Oral bioavailability and brain penetration of (-)-stepholidine, a tetrahydroprotoberberine agonist at dopamine D(1) and antagonist at D(2) receptors, in rats. Br J Pharmacol. Nov. 2009;158(5):1302-12. Epub Sep. 25, 2009.

Szajewska, H. Evidence-based medicine and clinical research: both are needed, neither is perfect. Ann Nutr Metab. 2018;72 Suppl 3:13-23. doi: 10.1159/000487375. Epub Apr. 9, 2018. PMID: 29631266.

Wesserling et al., Will in vitro tests replace animal models in experimental oncology? J Tissue Scie Eng. 2011; 2:102e. doi:10. 4172/2157-7552.1000102e.

Wolff, M.E. Burger's Medicinal Chemistry and Drug Discovery. vol. 1, Principles and Practice, Fifth Edition. John Wiley & Sons 1995. pp. 975-977.

Ugrumov M.V., Development of preclinical diagnosis and preventive treatment of neurodegenerative diseases. Zh Nevrol Psikhiatr Im S S Korsakova. 2015;115(11):4-14. Russian. doi: 10.17116/jnevro20151151114-14.

U.S. Appl. No. 16/198,917, filed Nov. 23, 2018, Granted, U.S. Pat. No. 10,729,710.

U.S. Appl. No. 16/872,802, filed May 12, 2020, Granted, U.S. Pat. No. 11,110,110.

U.S. Appl. No. 17/386,686, filed Jul. 28, 2021, Granted, U.S. Pat. No. 11,707,476.

U.S. Appl. No. 18/330,293, filed Jun. 6, 2023, Pending, N/A.

U.S. Appl. No. 16/876,843, filed May 18, 2020, Granted, U.S. Pat. No. 11,104,697.

U.S. Appl. No. 16/876,878, filed May 18, 2020, Granted, U.S. Pat. No. 11,111,263.

U.S. Appl. No. 17/391,439, filed Aug. 2, 2021, Allowed, 2022-0194978.

U.S. Appl. No. 16/876,908, filed May 18, 2020, Granted, U.S. Pat. No. 11,130,775.

U.S. Appl. No. 17/392,970, filed Aug. 3, 2021, Allowed, 2022-0024962.

U.S. Appl. No. 16/876,966, filed May 18, 2020, Granted, U.S. Pat. No. 11,168,056.

U.S. Appl. No. 17/495,997, filed Oct. 7, 2021, Allowed, 2022-0024875.

U.S. Appl. No. 18/359,136, filed Jul. 26, 2023, Pending, N/A.

U.S. Appl. No. 17/606,313, filed Oct. 25, 2021, Published, 2022-0213136.

U.S. Appl. No. 17/606,319, filed Oct. 25, 2021, Published, 2022-0213071.

U.S. Appl. No. 17/606,332, filed Oct. 25, 2021, Published, 2022-0213040.

U.S. Appl. No. 17/606,303, filed Oct. 25, 2021, Published, 2022-0220077.

U.S. Appl. No. 18/036,596, filed May 11, 2023, Pending, N/A.

Elger et al., Estrogen sulfamates: a new approach to oral estrogen therapy. Reprof Fertil Dev. 2001;13(4)297-305. doi: 10.1071/rd01029.

Elger et al., Novel estrogen sulfamates: a new approach to oral hormone therapy. Expert Opin Investig Drugs. Apr. 1998;7(4)575-89. doi: 10.1517/13543784.7.4.575.

Elger et al., Sulfamates of various estrogens are prodrugs with increased systemic and reduced hepatic estrogenicity at oral application. J Steroid Biochem Mol Biol. Dec. 1995;55(3-4):395-403. doi: 10.1016/0960-0760(95)00214-6.

Malmquist et al., The synthesis of tritiated (R)-2-methoxy-N-n-propyl-nor-apomorphine (MNPA). J Label Compd Radiopharm. Sep. 2007;50(13):1211-1214.

\* cited by examiner

FIGURES

PROCESS FOR THE MANUFACTURE OF (2S,3S,4S,5R,6S)-3,4,5-TRIHYDROXY-6-(((4AR,10AR)-7-HYDROXY-1-PROPYL-1,2,3,4,4A,5,10,10A-OCTAHYDROBENZO[G]QUINOLIN-6-YL)OXY)TETRAHYDRO-2H-PYRAN-2-CARBOXYLIC ACID

CROSS-REFERENCE TO RELATED APPLICATION

This application is a continuation application of U.S. application Ser. No. 16/876,843, filed May 18, 2020, which claims priority to Danish Application No. PA201900598, filed May 20, 2019. The entire contents of the aforementioned applications are hereby incorporated herein by reference.

FIELD OF THE INVENTION

The present invention relates to a process for manufacturing (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid which is a compound for use in the treatment of neurodegenerative diseases and disorders such as Parkinson's Disease. The invention also relates to new intermediates of said process and the process of manufacturing said intermediates.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striato-pallidal 'indirect pathway' express D2 receptors (MSN-2); whereas GABAergic-MSN projecting to the substantia nigra pars reticulata and internal pallidum, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxy phenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

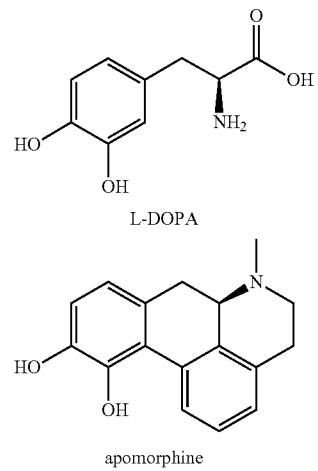

L-DOPA apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include 1) dyskinesia which are abnormal involuntary movements occurring during the optimal 'on-time effect' of the drug; and 2) off fluctuations, period during which the L-DOPA positive effect wears off and symptoms re-emerge or worsen (Sprenger and Poewe, CNS Drugs (2013), 27: 259-272).

Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-noraporphine (NPA) and the mono pivaloyl ester of apomorphine for duodenal delivery (see e.g. WO 02/100377), and the D1-like agonist adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-dioxy derivative or di-acetalyl derivative. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-Propyl-1,2,3,4,4a,5,10,10a-octahydro-benzo[g]quinoline-6,7-diol depicted as compound (I) below is disclosed in WO 2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

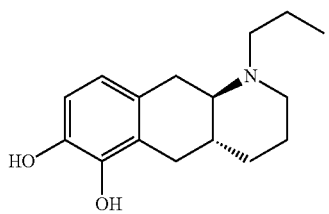

(I)

Compound (1) is a dopamine receptor agonist with mixed D1 and D2 activity. Some prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

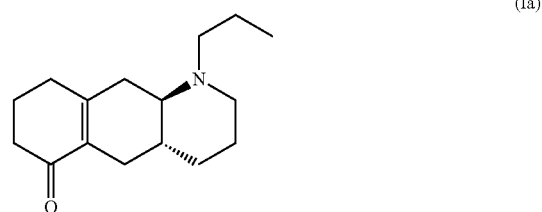

(Ia)

WO 2009/026934 and WO 2009/026935 disclose two types of prodrug derivatives of compound (I) including a compound with the formula (Ib) below:

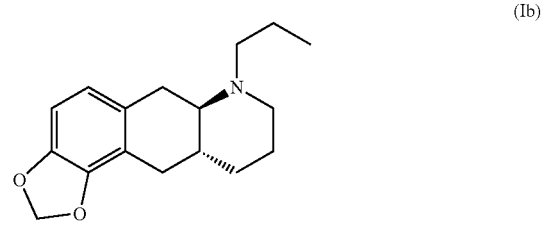 [SMILES: CCCN1CCC[C@@H]2Cc3c(ccc4c3OCO4)C[C@H]21]

(Ib)

The conversion of compound (Ib) to compound (I) in rat and human hepatocytes has been demonstrated in WO 2010/097092. Furthermore, the in vivo pharmacology of the compounds (Ia) and (Ib) as well as the active "parent compound" (1) has been tested in various animal models relevant for Parkinson's Disease (WO 2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO 2009/026934 and WO 2009/026935 is a conventional ester prodrug of the formula (Ic):

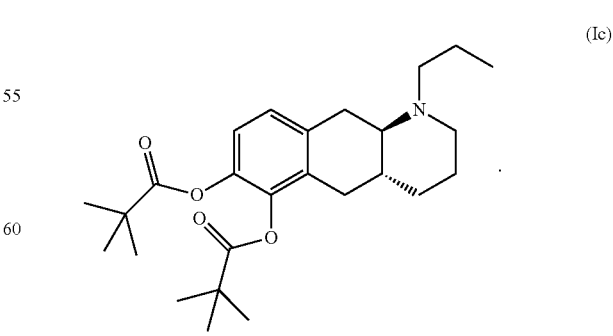

(Ic)

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

Consequently, there is also a need for a process for manufacturing of such drugs, particularly processes that are suitable for large scale production and resulting in a high yield of the compound of formula (Id).

SUMMARY OF THE INVENTION

The present invention relates to a novel process for the manufacture of (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below

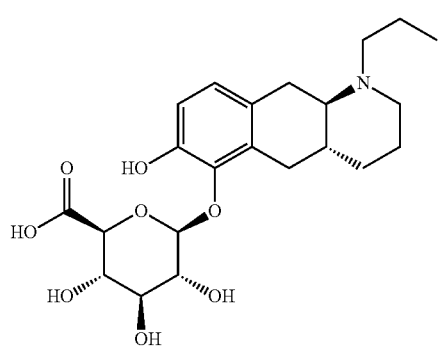

(Id)

from the compound (4aR,10aR)-1-Propyl-1,2,3,4,4a,5,10,10a-octahydro-benzo[g]quinoline-6,7-diol with the formula (I) below

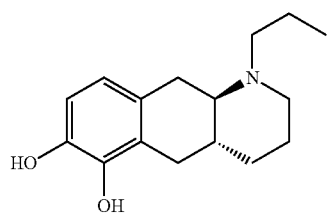

(I)

The overall process starting from compound (I) is illustrated in scheme 1 below.

Scheme 1 Overview of overall process

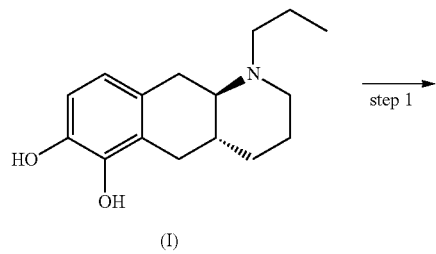

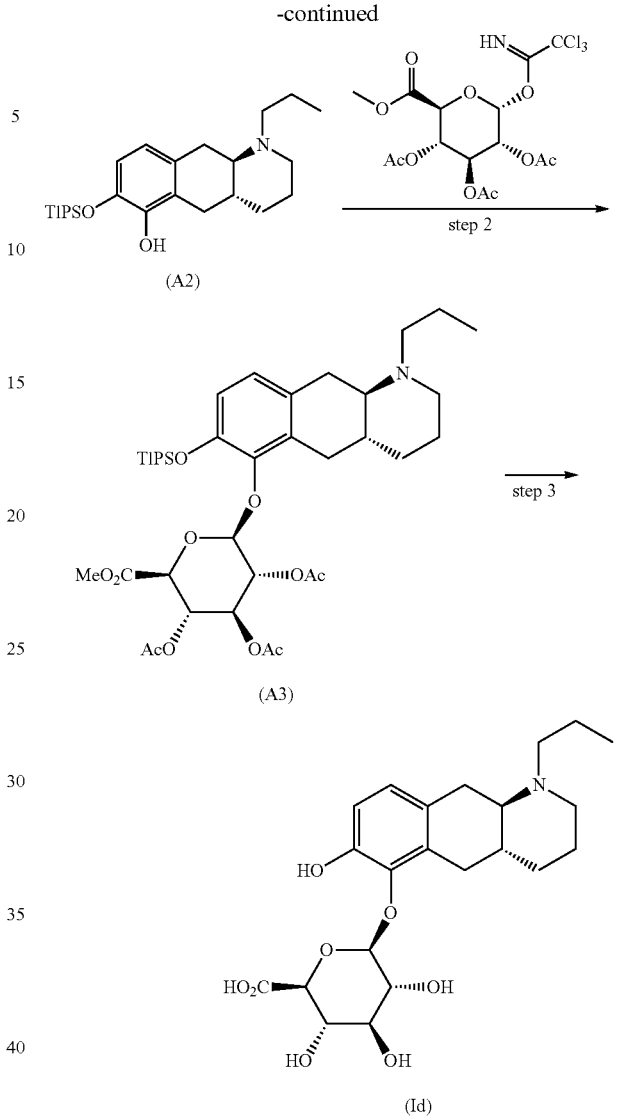

In an embodiment, the invention relates to a process for the preparation of compound (Id), or a pharmaceutically acceptable salt thereof from compound (I), wherein said process comprises the following step 2) reacting compound (A2) with (2S,3S,4S,5R,6R)-2-(methoxycarbonyl)-6-(2,2,2-trichloro-1-iminoethoxy)tetrahydro-2H-pyran-3,4,5-triyl triacetate to obtain compound (A3) according to the reaction scheme 2.

Scheme 2 Overview of step 2

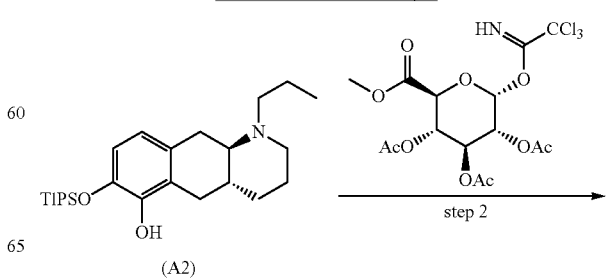

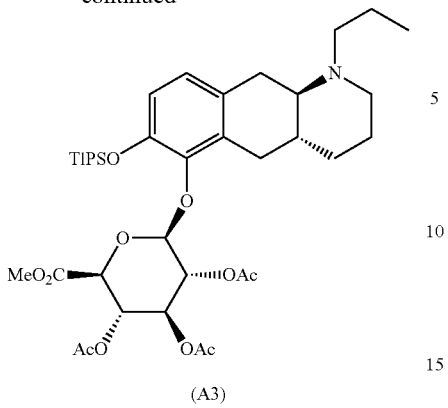

(A3)

wherein said reaction takes place in an aprotic solvent in the presence of a Lewis acid.

In an embodiment, the invention relates to the compound of formula (A3) below

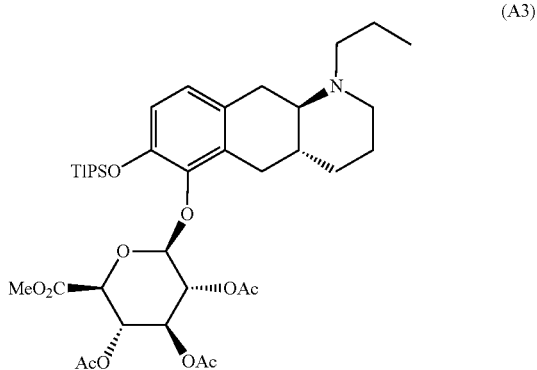

(A3)

or a salt thereof.

In an embodiment, the invention relates to a process for the preparation of compound (Id), or a pharmaceutically acceptable salt thereof from compound (I)

wherein said process comprises the following step 3) deprotecting compound (A3) by contacting compound (A3) with a nucleophilic reagent to obtain compound (Id), or a pharmaceutically acceptable salt thereof according to the reaction scheme 3.

In a specific embodiment of the invention, the nucleophilic reagent used in step 3 is a base e.g. KOH or NaOH.

Scheme 3 Overview of step 3

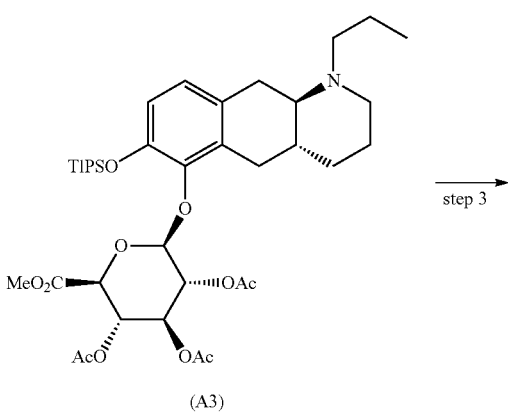

(A3)

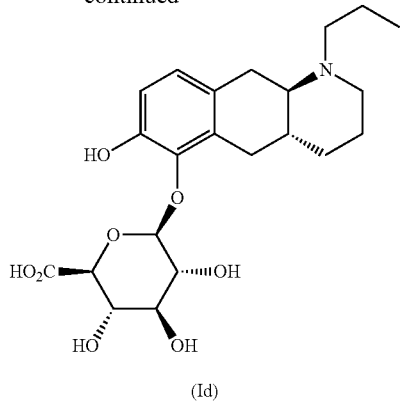

(Id)

Individual aspects of the invention relate to each of the process steps 1), 2), and 3).

Other individual aspects of the invention relate to new intermediates of the process. Thus, further aspects of the present invention relate to compounds (A2) and (A3) and salts thereof respectively, which are useful intermediates in the processes for the manufacturing of the compound (Id), or a pharmaceutically acceptable salt thereof.

The overall process, as well as each individual process step and intermediates as provided by the invention are useful for large scale production of compound (Id), or a pharmaceutically acceptable salt thereof.

Definitions

References to Compounds

References to compound (I), compound (Id), (A2) and (A3) include compounds in solution and solid forms of the compounds including the free substance (zwitter ion) of said compounds, salts of said compounds, such as acid addition salts or base addition salts, and polymorphic and amorphous forms of compounds of the invention and of salts thereof. Furthermore, said compounds and salts thereof may potentially exist in unsolvated as well as in solvated forms with solvents such as water, ethanol and the like.

Pharmaceutically Acceptable Salts

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Compounds of the invention may be used as intermediates for the manufacture of compound (Id)), or a pharmaceutically acceptable salt thereof. Hence, the salt form of the intermediates disclosed herein are not limited to pharmaceutically acceptable salts thereof. Nevertheless, pharmaceutically, acceptable salts of the intermediates can also advantageously be used in the manufacture of compound (Id), or a pharmaceutically acceptable salt thereof. Hence, in an embodiment of the invention the salt of compound (I), A2, A3, or compound (Id) is a pharmaceutically acceptable salt.

Prodrug

In the present context, the terms "prodrug" or "prodrug derivative" indicates a compound that, after administration to a living subject, such as a mammal, preferably a human, is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-1-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of the compound of formula (Id) is understood to be the compound of formula (I).

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of the compound of formula (Id), using non-compartmental modelling. Abbreviated PK parameters are: $C_{max}$ (maximum concentration); $t_{max}$ (time to $C_{max}$); $t_{1/2}$ (half-life); $AUC_{0-24}$ (area under the curve from time of dosing and 24 hours after dosing), and "Exposure at 24 h" is the concentration measured 24 hours after dosing.

Therapeutically Effective Amount

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject.

In the context of the present invention, a "therapeutically effective amount" of the compound of formula (Id) indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment

The compound prepared by the process of the present invention is intended for treatment of neurodegenerative or neuropsychiatric diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compound of formula (Id).

The invention encompasses use of the compound of formula (Id) obtained by a process of the invention for treatment of the diseases and disorders listed above.

Administration Routes

Pharmaceutical compositions comprising a compound of formula (Id), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising the compound of formula (Id), i.e. the compound (Id), or a pharmaceutically acceptable salt thereof directly obtained by the process of the invention, for example as disclosed in the Experimental Section herein. The present invention also provides a process for making a pharmaceutical composition comprising a compound of formula (Id), or a pharmaceutically acceptable salt thereof such as compound (Id), or a pharmaceutically acceptable salt thereof directly obtained by the process of the invention. The pharmaceutical compositions according to the invention may be formulated with pharmaceutically acceptable excipients in accordance with conventional techniques such as those disclosed in Remington, "The Science and Practice of Pharmacy", 22$^{th}$ edition (2013), Edited by Allen, Loyd V., Jr.

The pharmaceutical composition comprising a compound of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses

In one embodiment, compound (Id), or a pharmaceutically acceptable salt thereof obtained by a process of the invention is administered in an amount from about 0.0001 mg/kg body weight to about 5 mg/kg body weight per day. In particular, daily dosages may be in the range of 0.001 mg/kg body weight to about 1 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a compound of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

X-axis: time (hours); Y-axis: plasma concentration of Compound (1) (µg/mL) obtained after dosing of the following compounds 0: compound (Ia); A: compound (Ib); +: compound (Id).

Figure 2:
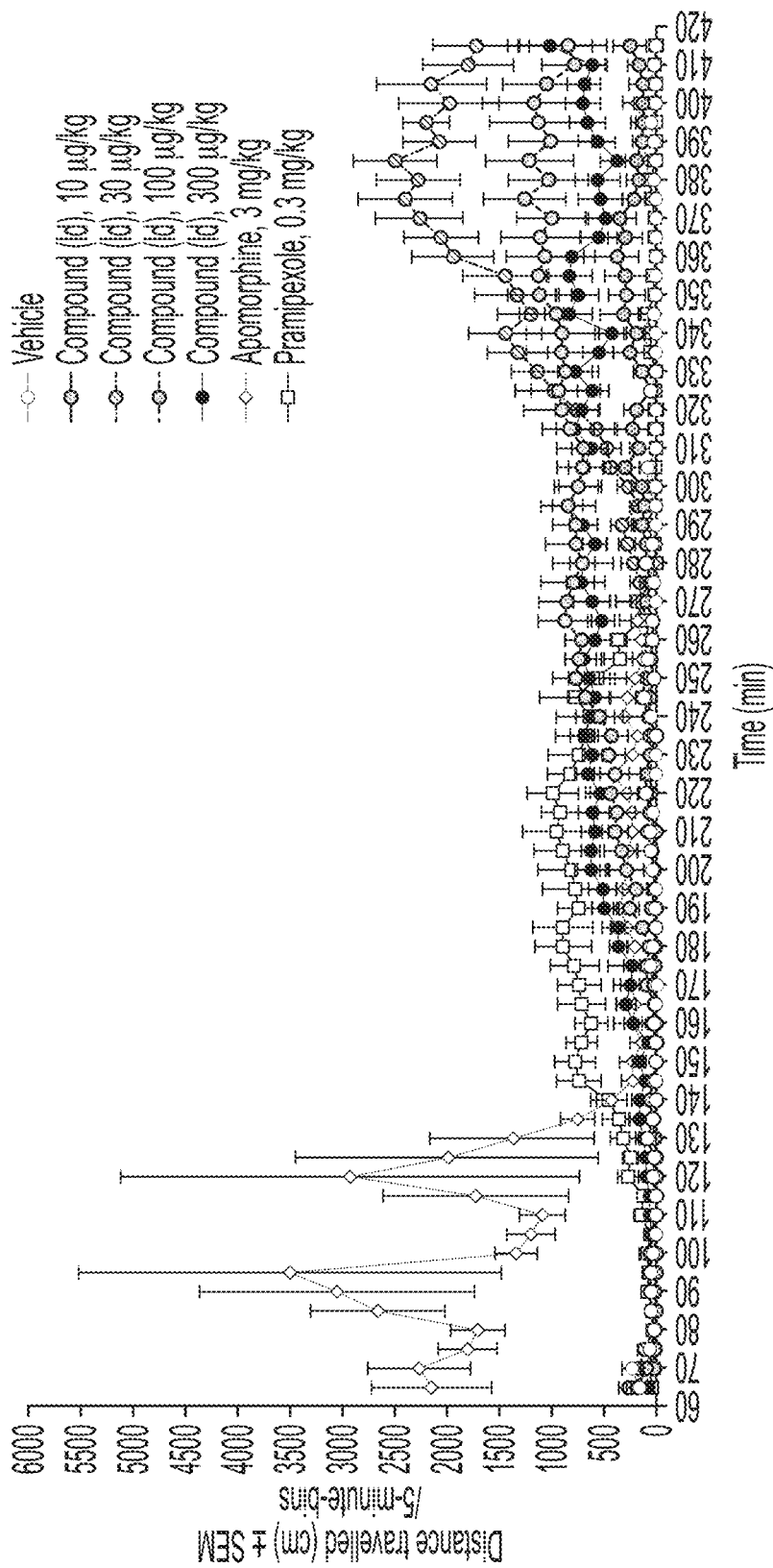
Figure 3:
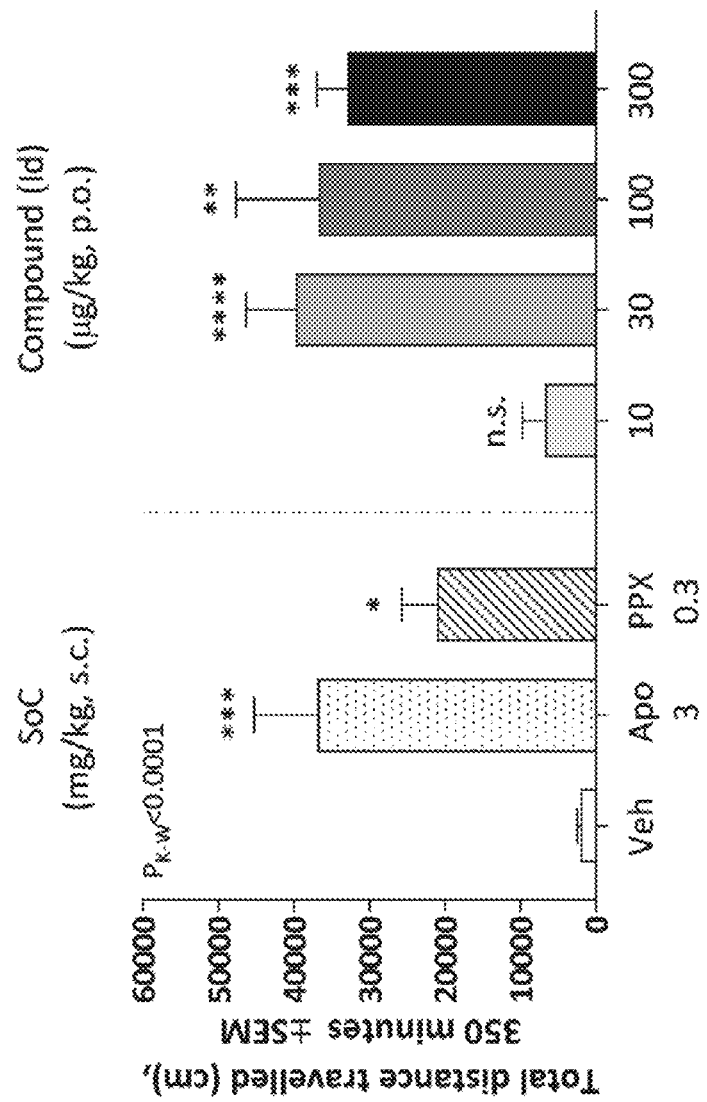

FIGS. 2-3: Locomotor activity time-course (FIG. 2) and total distance travelled (FIG. 3) following treatment with vehicle (H$_2$O, p.o.), or compound (Id) (10, 30, 100 or 300 µg/kg, p.o.) and compared to standard-of-care (SoC) treatments: apomorphine (APO, 3 mg/kg, s.c.), pramipexole (PPX, 0.3 mg/kg, s.c.). Animals were dosed at t=60 minutes after a 60-minutes habituation period in test chambers, and activity was monitored for 350 minutes thereafter. Data was evaluated by use of a Kruskal-Wallis test with Dunn's Multiple Comparisons test, resulting in an overall P-value of <0.0001.

FIG. 2: X-axis: time (min); Y-axis: Distance travelled (cm) ±SEM/5-minute-bins

FIG. 3: Y-axis: Total distance travelled (cm) ±SEM. Significance levels for post-hoc comparisons (relative to the vehicle group) are indicated: *<0.05, <0.01, *<0.001, ****<0.0001.

Figure 4:
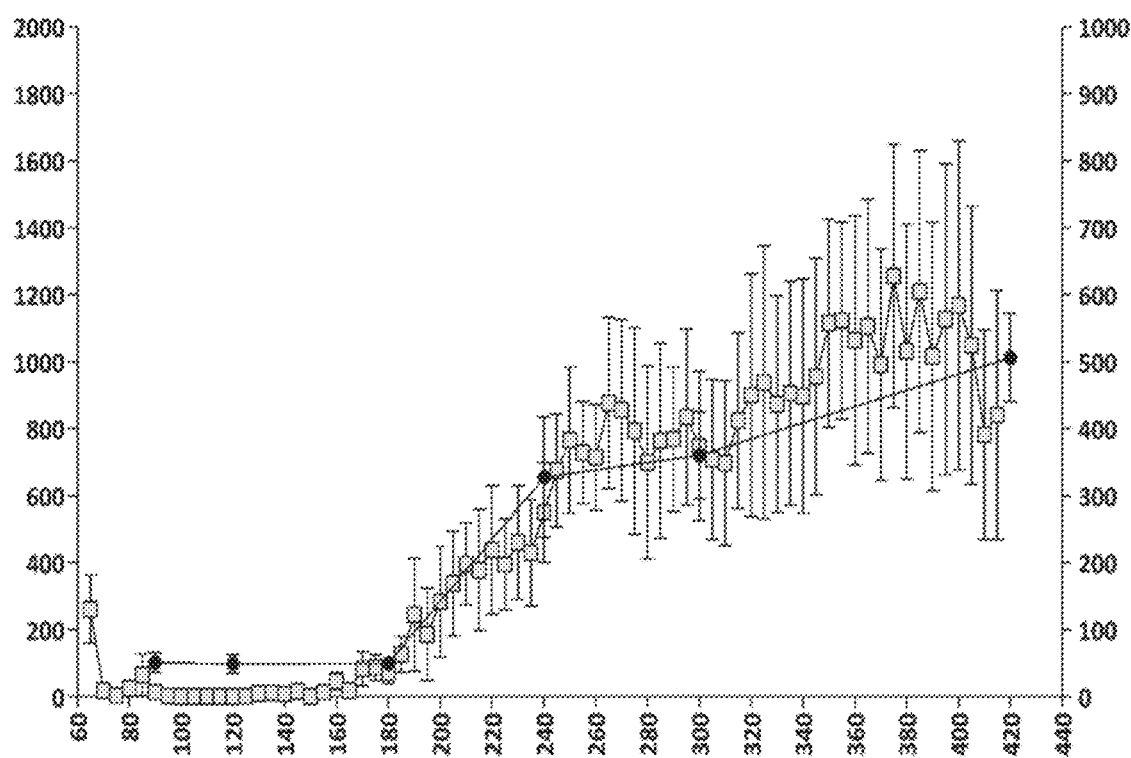
Figure 5:
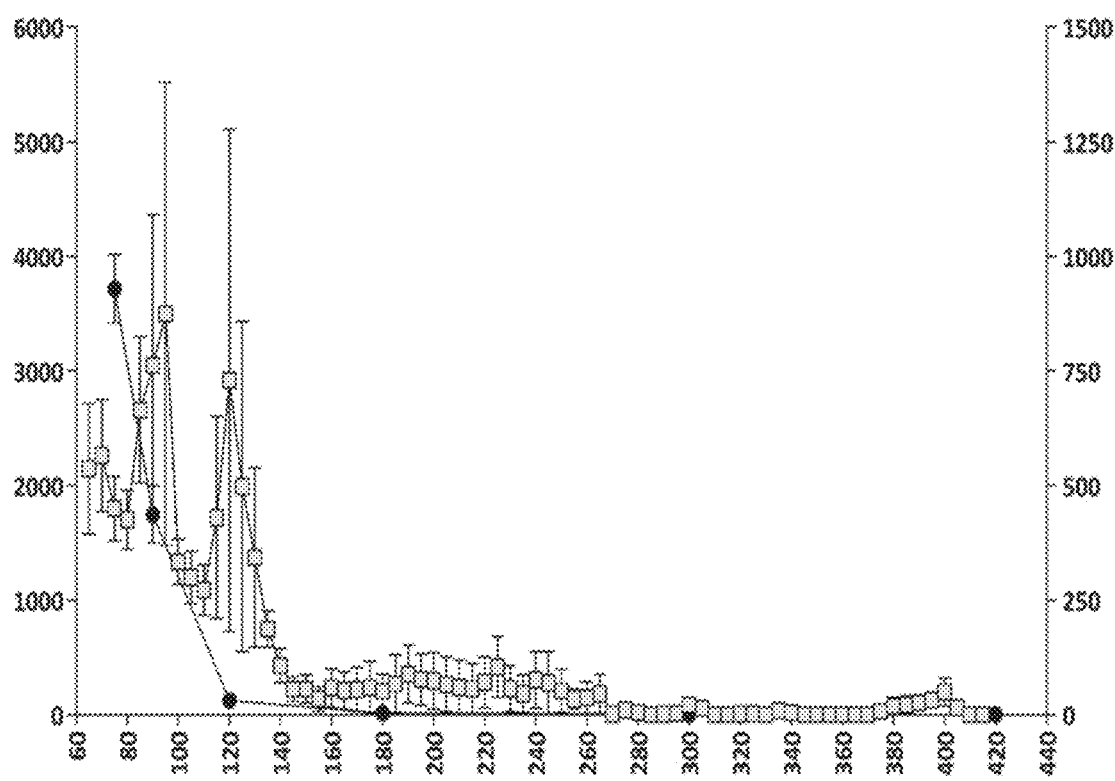

FIGS. 4-5: Relationships between plasma concentrations of compound (Id) and compound (I) and hyperactivity induced by compound (Id) (100 µg/kg, p.o.) (FIG. 4) and the corresponding relationship between plasma apomorphine concentrations and hyperactivity induced by apomorphine (3 mg/kg, s.c.) (FIG. 5).

X-axis time (min); Y-axis left: Distance travelled (cm) ±SEM/5-minute-bins; Y-axis right (FIG. 4): plasma concentration of compound (I) (μg/mL); Y axis right (FIG. 5): plasma concentration of apomorphine (ng/mL).

□: Distance traveled (cm)• plasma concentration.

Figure 6A:
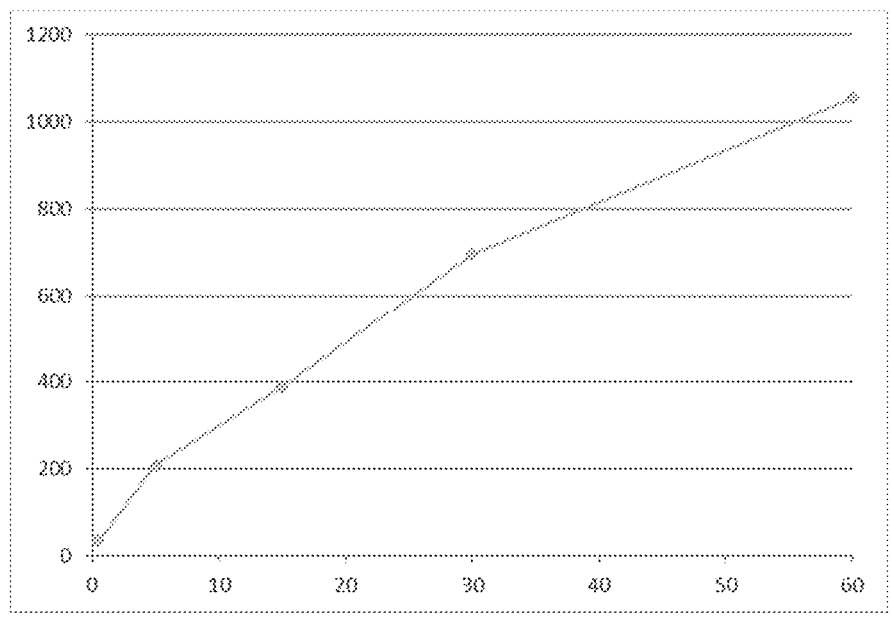
Figure 6B:
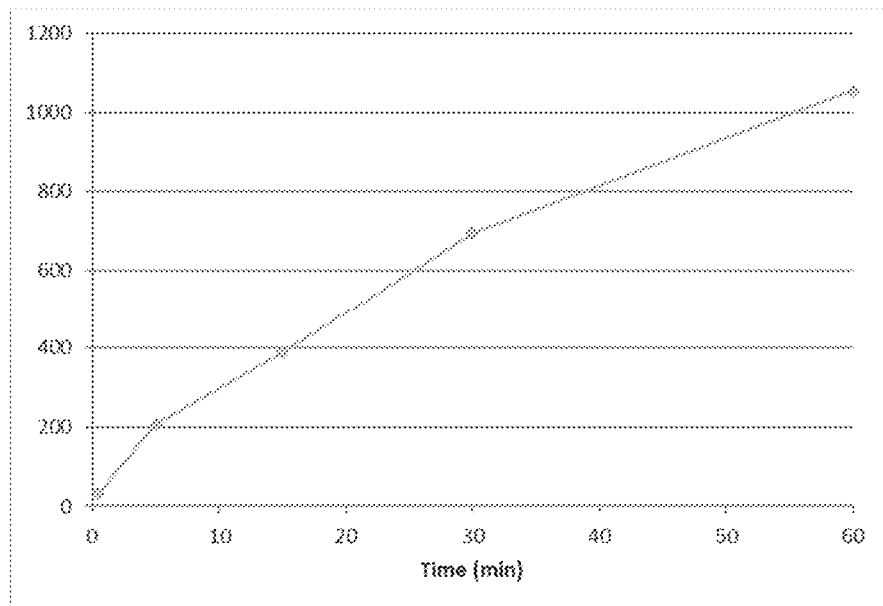

FIG. 6: Conversion of compound (Id) to compound (I) in rat (FIG. 6A) and human (FIG. 6B) hepatocytes.

X-axis time (min); Y-axis: concentration of compound (I) (μg/mL).

Figure 7A:
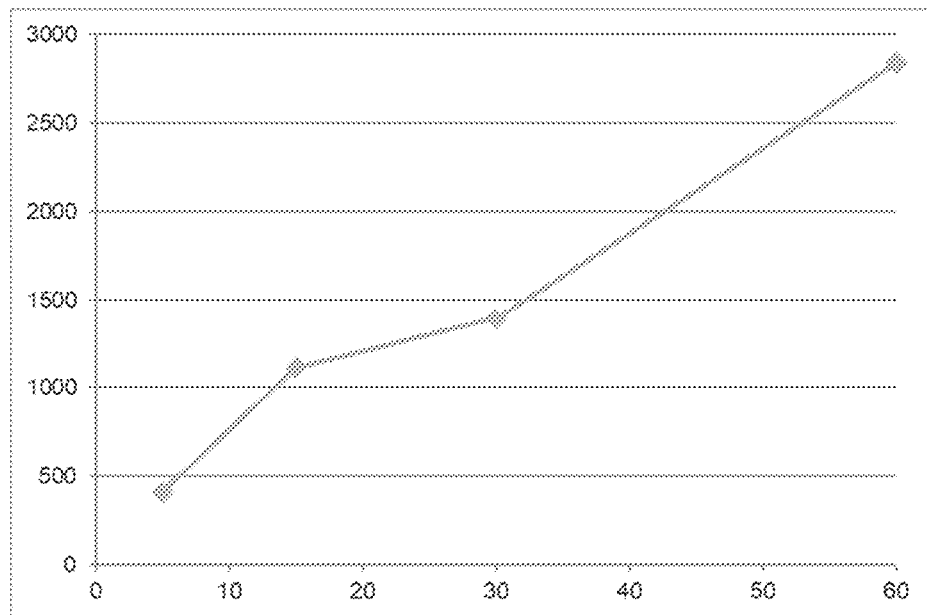
Figure 7B:
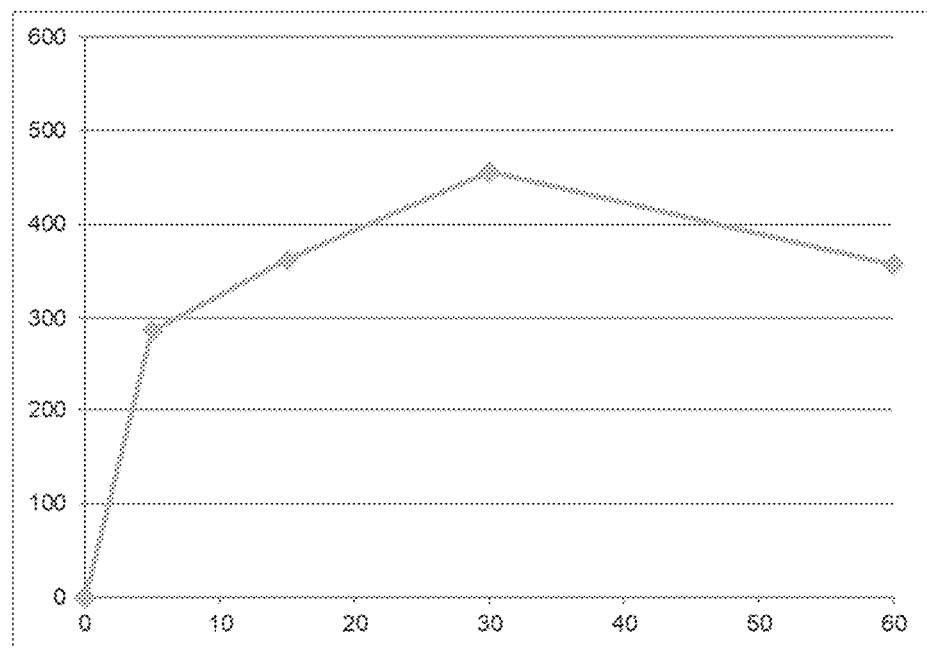

FIG. 7: Conversion of compound (Id) in rat (FIG. 7A) and human (FIG. 7B) whole blood.

X-axis time (min); Y-axis: concentration of compound (I) (μg/mL).

DETAILED DESCRIPTION OF THE INVENTION

The present invention relates to a process for manufacturing the compound (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below and salts thereof

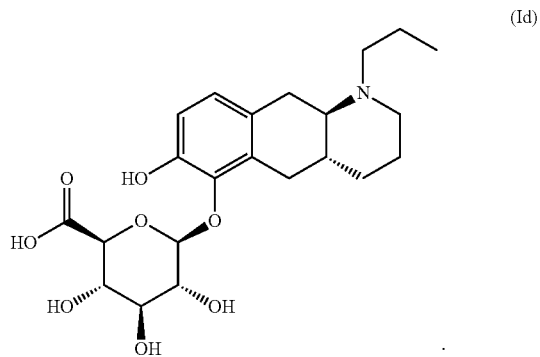 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id)

The compound of formula (Id) is a prodrug of (4aR,10aR)-1-Propyl-1,2,3,4,4a,5,10,10a-octahydro-benzo[g]quinoline-6,7-diol [compound (I)] which is a dual D1/D2 agonist with in vitro data listed in Table 2.

The inventors have observed that compound (I) is conjugated in rat and human hepatocytes to sulfate and glucuronide derivatives including compound (Id). The conjugates have shown to be converted to compound (I) by conjugation and de-conjugation in the body.

Glucuronide and sulfate derivatives are commonly known to be unstable in the intestine. The derivatives are formed as highly polar and soluble metabolites to facilitate the elimination of compounds from the body and are consequently easily excreted. For example, in bile duct cannulated rats, glucuronide and sulfate conjugates are often found in bile while their de-conjugate (i.e. the parent compound) is found in faeces. The back-conversion of glucuronide and sulfate conjugates in the intestine to the parent compound which is then sometimes subsequently reabsorbed, is known as part of the enterohepatic re-circulation process. As mentioned earlier, oral dosing of phenethyl catecholamines, such as apomorphine, has generally proven unsuccessful due to low bioavailability. Likewise, compound (I) suffers from low oral bioavailability (Liu et al., Bioorganic Med. Chem. (2008), 16: 3438-3444). With this in mind and considering the instability of glucuronide and sulfate conjugates in the gastrointestinal tract, it would not be expected that oral dosing of glucuronide conjugates of compound (I) can be used to achieve sufficient plasma exposure of the compound.

The principle of applying glucuronide derivatives as prodrugs for oral delivery has been explored for retinoic acid (Goswami et al., J. Nutritional Biochem. (2003) 14: 703-709) and for morphine (Stain-Texier et al., Drug Metab. and Disposition (1998) 26 (5): 383-387). Both studies showed very low exposure levels of the parent compounds after oral dosing of the derivatives. Another study suggests the use of budenoside-β-D-glucuronide as a prodrug for local delivery of budenoside to the large intestine for treatment of Ulcerative Colitis based on poor absorption of the prodrug itself from the intestinal system (Nolen et al., J. Pharm Sci. (1995), 84 (6): 677-681).

Nevertheless, surprisingly, it has been observed that oral dosing of compound (Id) which has been identified as a metabolite of compound (I) in rats and minipigs provides a systemic exposure of compound (I) in plasma, suggesting the usefulness of said compound as an orally active prodrug of compound (I).

Figure 1:
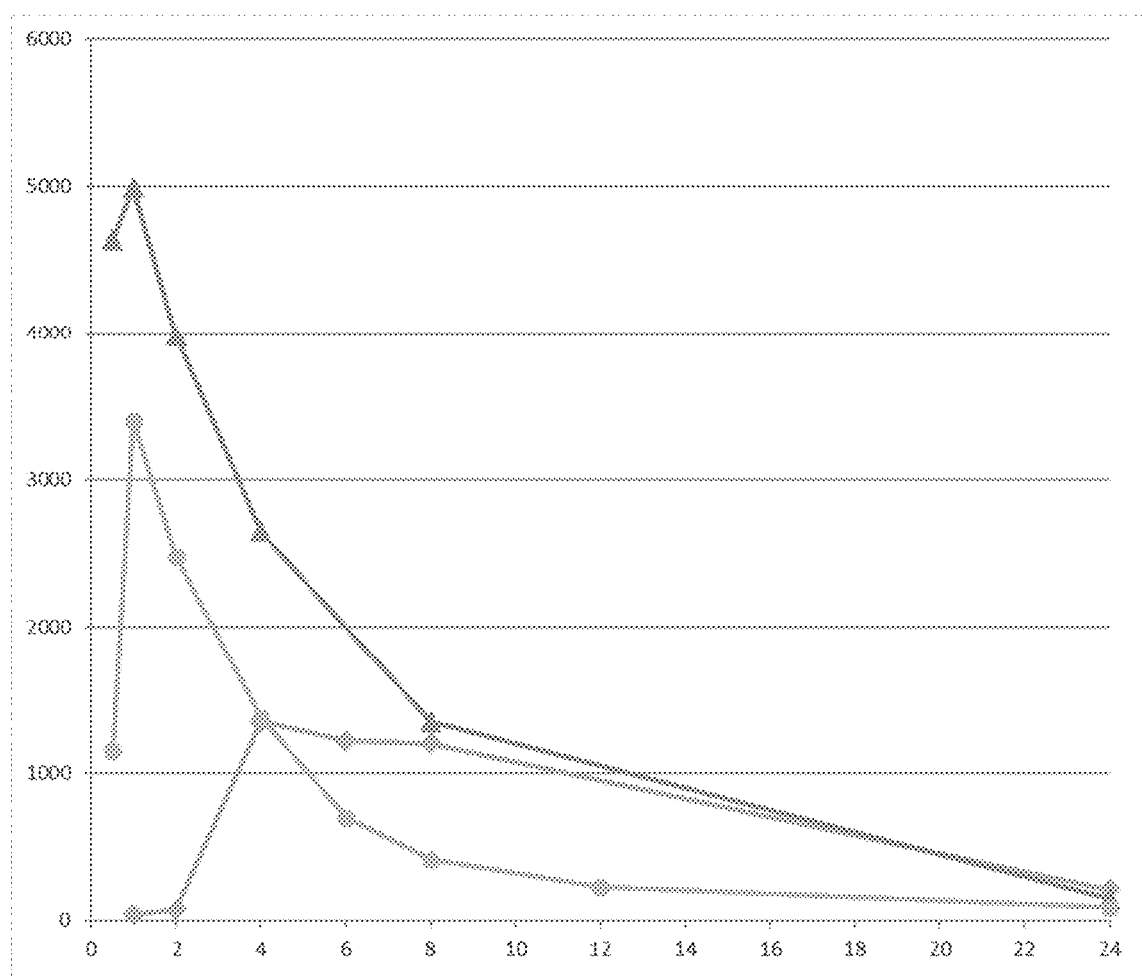
FIG. 1: PK profiles in Wistar rats obtained after oral dosing according to Example 7. Profiles are based on mean plasma concentrations from 3 subjects for each compound.

The plasma profile of compound (I) resulting from oral dosing of compounds (Ia) and (Ib) and compound (Id) to Wistar rats according to Example 7 are shown in FIG. 1. For all the compounds, the doses were corrected by molecular weight to equal a dose of 300 μg/kg of compound (Ib) corresponding to 287 μg/kg of compound (I). The inventors have found that oral dosing of compounds (Ia) and (Ib) to Wistar rats results in early and high peak concentrations of compound (I). Such high peak concentrations are in humans likely to be associated with dopaminergic side effects such as for example nausea, vomiting and light headedness. In contrast, dosing of the compound (Id), results in a slower absorption rate avoiding rapid peak concentrations accompanied by a sustained exposure of compound (I) in plasma. Additionally, the plasma exposure of compound (I) in Wistar rats is maintained throughout 24 hours although the obtained AUC of compound (I) is generally lower than the AUC obtained after dosing of compound (Ib). However, since the peak concentrations of compound (I) which are expected to drive the side effects are lower, higher doses might be administered of the compound (Id) to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability demonstrated for the compound of formula (Id) was highly unpredictable. PK parameters for the PK studies in Wistar rats are listed in Table 3.

In vivo conversion of compound (Id) to compound (I) has also been observed by after oral dosing of compound (Id) in minipigs.

Bioconversion of compound (Id) in human is supported by the Experiments of Example 4a and Example 4b indicating conversion to the compound of formula (I) in rat and human hepatocytes and in rat and human blood (FIGS. 6 and 7).

Thus, in conclusion, the compound of formula (Id) is useful as an orally active prodrug of compound (I) and has been observed in rats to provide a PK profile avoiding the peak $C_{max}$ observed for the known prodrugs (Ia) and (Ib) and providing a significantly higher AUC of compound (I) than compound (Ic).

Compound (Id) has further been explored in the rat locomotor activity assay according to Example 8. The assay demonstrated a dopaminergic effect obtained after oral administration of compound (Id) c.f. FIGS. 2, 3 and 4. The fact that the compound of formula (Id) possesses no in vitro dopaminergic activity c.f. example 5 and table 2, further indicates that the effect of compound (Id) in the rat locomotor activity assay is obtained by conversion of compound (Id) to compound (I).

Finally, an important issue associated with the prior art compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of compound (Id) is that the compound is not a 5-HT2B agonists c.f. example 6 and Table 2.

The compound of formula (Id) is useful in the treatment of neurodegenerative diseases and disorders such as Parkinson's disease and/or other conditions for which treatment with a dopamine agonist is therapeutically beneficial. The compound, being suitable for oral administration has the potential of providing a new treatment paradigm in Parkinson's Disease.

The invention provides a scalable synthesis of compound (Id). A key step is a direct glucuronide coupling reaction on compound (A2) using (2S,3S,4S,5R,6R)-2-(methoxycarbonyl)-6-(2,2,2-trichloro-1-iminoethoxy)tetrahydro-2H-pyran-3,4,5-triyl triacetate as the coupling donor. The invention also comprises a deprotection step utilizing sodium hydroxide in methanol/water thereby avoiding the use of for example toxic KCN. The overall process starting from compound (I) is illustrated in brief in scheme 4 below.

Scheme 4 Overall process

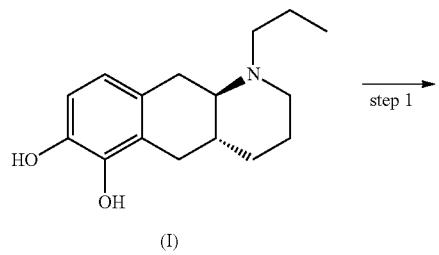

(I)

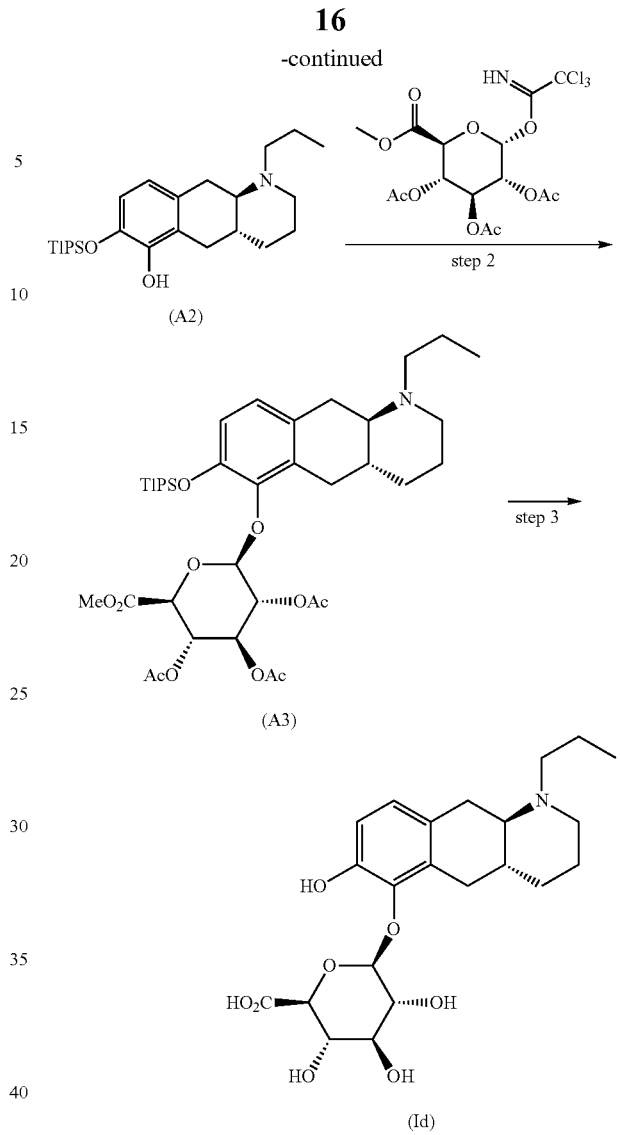

A process for the preparation of compound (I) to be used in step 1) has been disclosed in WO 2009/026934. WO2019/101917 discloses a process for preparation of the compound A2 and compound (Id).

Table 1 below provide an overview of the compounds (A2) and (A3) which are intermediates with the following respective compound names:

TABLE 1

Overview of intermediates

| Abbreviated name | Chemical Name | Structure drawing |
| --- | --- | --- |
| (A2) | (4aR,10aR)-1-propyl-7-((triisopropylsilyl)oxy)-1,2,3,4,4a,5,10,10a-octahydrobenzo[g]quinolin-6-ol | |

TABLE 1-continued

Overview of intermediates

| Abbreviated name | Chemical Name | Structure drawing |
|---|---|---|
| (A3) | (2S,3S,4S,5R,6S)-2-(methoxycarbonyl)-6-(((4aR,10aR)-1-propyl-7-((triisopropylsilyl)oxy)-1,2,3,4,4a,5,10,10a-octahydrobenzo[g]quinolin-6-yl)oxy)tetrahydro-2H-pyran-3,4,5-triyl triacetate | 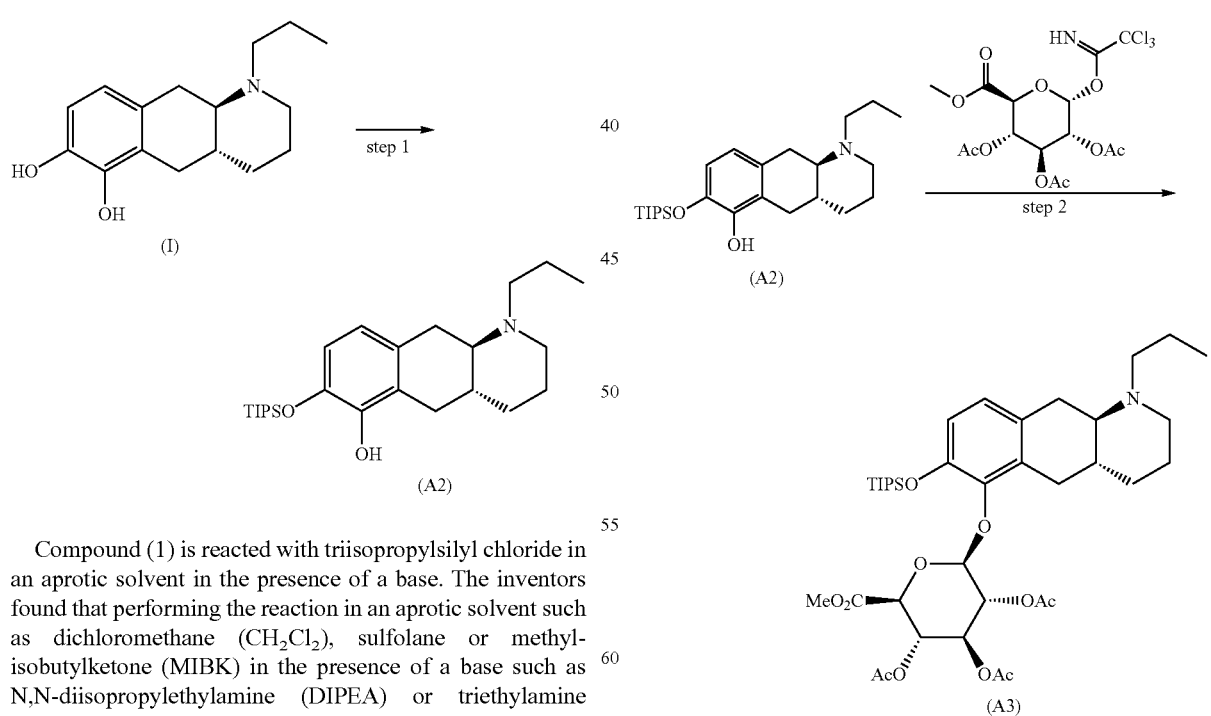 |

The reactant triisopropylsilyl chloride, used in step 1), can be purchased at Sigma-Aldrich (CAS Number: 13154-24-0).

The reactant (2S,3S,4S,5R,6R)-2-(methoxycarbonyl)-6-(2,2,2-trichloro-1-iminoethoxy)tetrahydro-2H-pyran-3,4,5-triyl triacetate, used in step 2), can be purchased at Sigma-Aldrich (CAS Number: 92420-89-8).

In Step 1) Compound (I) is Selectively Protected with a Triisopropylsilyl (TIPS) Protection Group to Afford the Compound (A2)

Compound (1) is reacted with triisopropylsilyl chloride in an aprotic solvent in the presence of a base. The inventors found that performing the reaction in an aprotic solvent such as dichloromethane ($CH_2Cl_2$), sulfolane or methyl-isobutylketone (MIBK) in the presence of a base such as N,N-diisopropylethylamine (DIPEA) or triethylamine resulted in a high conversion and selectivity. High conversion was observed when using 4-5 eq. DIPEA and performing the reaction at room temperature.

In one embodiment of the invention, step 1 is performed using dichloromethane ($CH_2Cl_2$) as solvent.

In another embodiment of the invention, step 1 is performed using sulfolane as solvent.

In yet another embodiment of the invention, step 1 is performed using methyl-isobutylketone (MIBK) as solvent.

In Step 2) Compound (A2) is Coupled with (2S,3S, 4S,5R,6R)-2-(methoxycarbonyl)-6-(2,2,2-trichloro-1-iminoethoxy)tetrahydro-2H-pyran-3,4,5-triyl triacetate

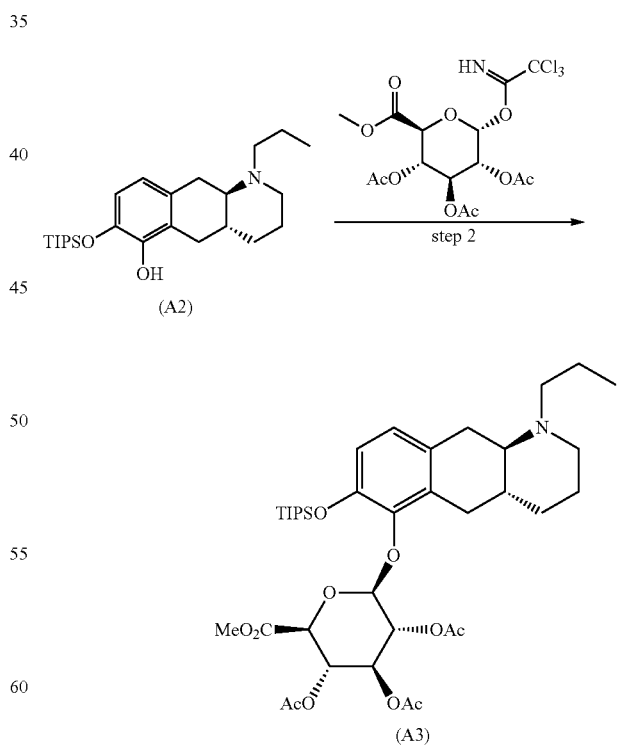

The reaction takes place in an aprotic solvent, preferably dichloromethane or benzotrifluoride, in the presence of a Lewis acid, preferably boron trifluoride diethyl etherate.

In Step 3) Compound (A3) is Deprotected Using a Suitable Nucleophilic Reagent to Afford Compound (Id) or a Pharmaceutically Acceptable Salt Thereof

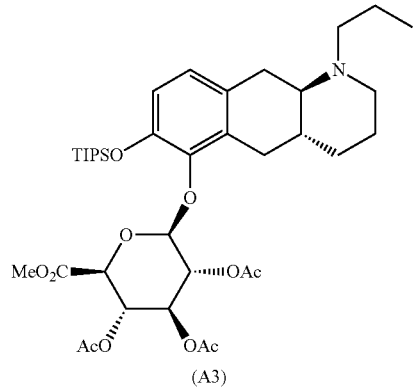

(A3)

step 3

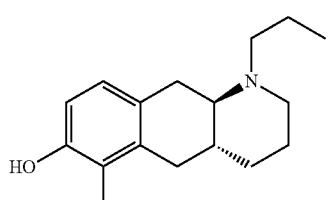

(Id)

The deprotection takes place in a solvent, for example a mixture of methanol (MeOH) and water, in the presence of a suitable nucleophilic reagent, for example a base, preferably a hydroxide base such as potassium hydroxide (KOH) or sodium hydroxide (NaOH).

In one embodiment, step 3) takes place in the presence of a solvent, such as a mixture of methanol (MeOH) and water.

In one embodiment of the invention, step 3 takes place using one or more suitable nucleophilic reagents, such as for example a hydroxide base and NH₄F. More specifically, step 3 may take place using a combination of NH₄F and potassium hydroxide (KOH) or sodium hydroxide (NaOH).

In a specific embodiment, step 3 takes place using potassium hydroxide (KOH) and NH₄F.

EMBODIMENTS OF THE INVENTION

In the following, embodiments of the invention are disclosed. The first embodiment is denoted E1, the second embodiment is denoted E2 and so forth.

E1. A process for the preparation of compound (Id) with the formula below

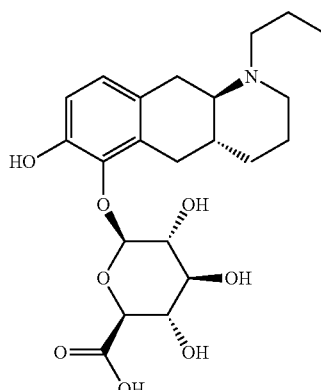

(Id)

from compound (I) with the formula below (I)

wherein said process comprises the following step
2) reacting compound (A2) with (2S,3S,4S,5R,6R)-2-(methoxycarbonyl)-6-(2,2,2-trichloro-1-iminoethoxy) tetrahydro-2H-pyran-3,4,5-triyl triacetate to obtain compound (A3) according to the reaction scheme below

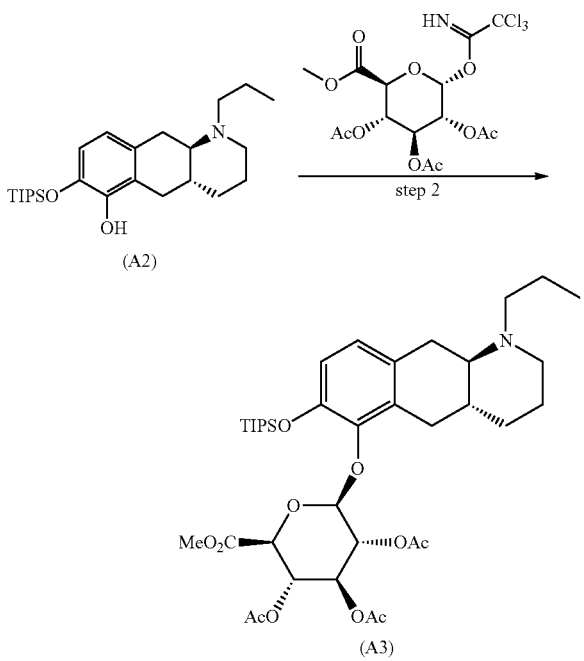

wherein said reaction takes place in an aprotic solvent in the presence of a Lewis acid.

E2. A process for the manufacturing of compound (A3) below comprising the following step
2) reacting compound (A2) with (2S,3S,4S,5R,6R)-2-(methoxycarbonyl)-6-(2,2,2-trichloro-1-iminoethoxy) tetrahydro-2H-pyran-3,4,5-triyl triacetate to obtain compound (A3) according to the reaction scheme below

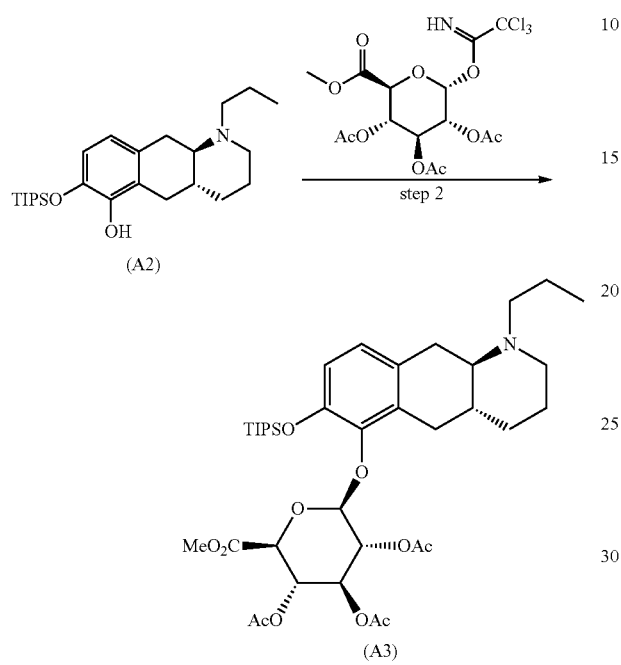

wherein said reaction takes place in an aprotic solvent in the presence of a Lewis acid.

E3. The process according to any of embodiments 1-2, wherein said aprotic solvent used in step 2) is dichloromethane.

E4. The process according to any of embodiments 1-3, wherein said Lewis acid used in step 2) is boron trifluoride diethyl etherate.

E5. The process according to any of embodiments 1-4, wherein said aprotic solvent is dichloromethane and said Lewis acid is boron trifluoride diethyl etherate.

E6. The compound of formula (A3) below

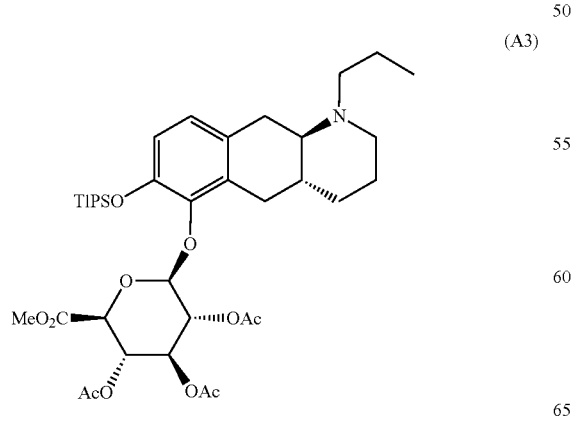

or a salt thereof.

E7. Use of a compound according to embodiment 6, in a process for the manufacture of the compound of formula (Id).

E8. A process for the preparation of compound (Id) with the formula below

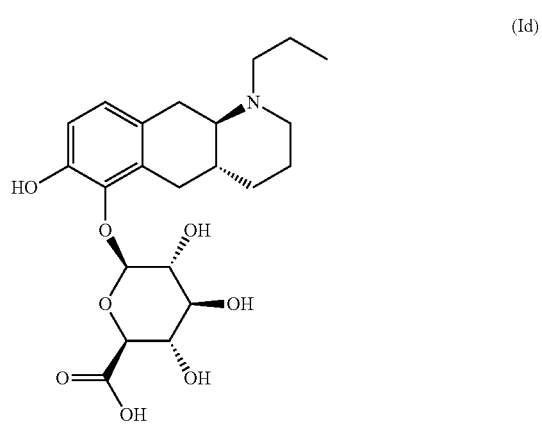 [SMILES: CCCN1CCC[C@@H]2Cc3c(ccc(O)c3O[C@@H]3O[C@H](C(=O)O)[C@@H](O)[C@H](O)[C@H]3O)C[C@H]21]

from compound (I) with the formula below

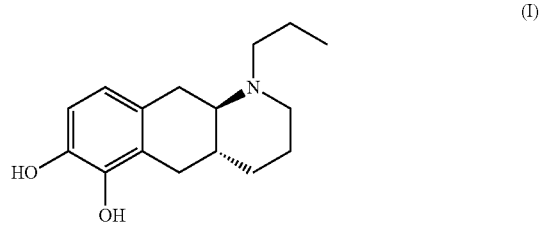 [SMILES: CCCN1CCC[C@@H]2Cc3c(ccc(O)c3O)C[C@H]21]

wherein said process comprises the following step 3) deprotecting compound (A3) by contacting compound (A3) with a base to obtain compound (Id) according to the reaction scheme below

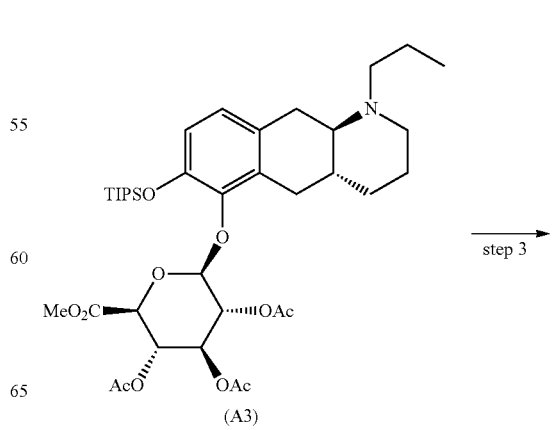

-continued

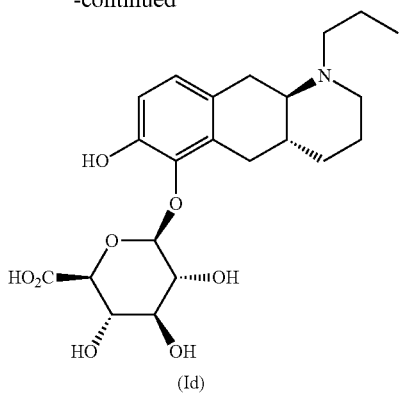
(Id)

E9. The process according to any of embodiments 1 and 3-5 wherein step 2) is followed by the following step
3) deprotecting compound (A3) by contacting compound (A3) with a base to obtain compound (Id) according to the reaction scheme below

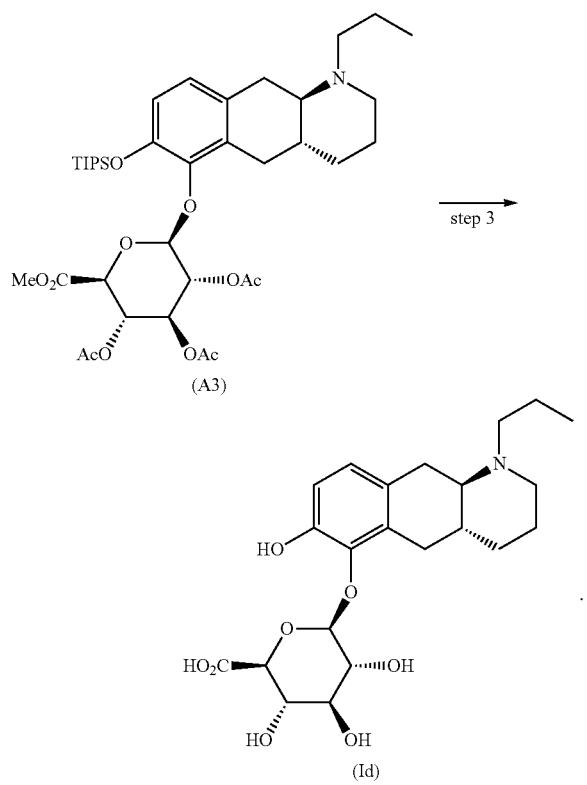

E10. The process according to any of embodiments 8-9, wherein said base used in step 3) is selected from potassium hydroxide and sodium hydroxide.

E11. The process according to any of embodiments 8-10, wherein said deprotection takes place in a mixture of methanol and water.

E12. The process according to any of embodiments 1-5 and 9-11, wherein compound (A2) has been obtained by the following step
1) reacting compound (I) with triisopropylsilyl chloride to obtain compound (A2) according to the reaction scheme below

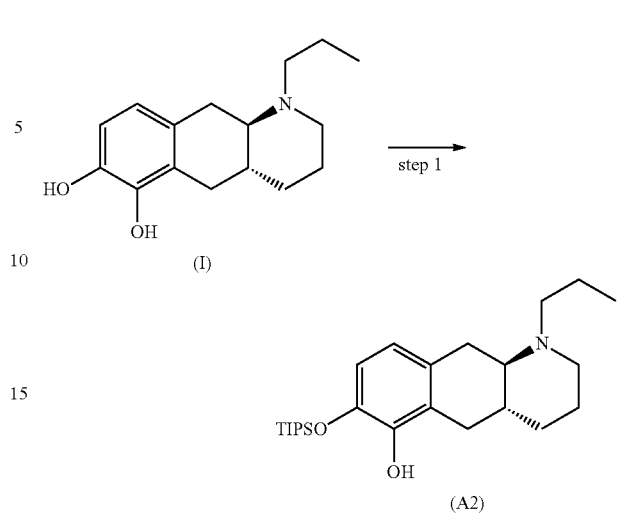

wherein the reaction takes place in an aprotic solvent in the presence of a base.

E13. The process according to embodiment 12, wherein said aprotic solvent used in step 1) is dichloromethane.

E14. The process according to any of embodiments 12-13, wherein said base used in step 1) is N,N-diisopropylethylamine (DIPEA).

E15. The process according to any of embodiments 12-14, wherein said aprotic solvent is dichloromethane and said base is N,N-diisopropylethylamine (DIPEA).

E16. The process according to any of embodiments 14-15, wherein said N,N-diisopropylethylamine (DIPEA) is present in an amount of 4-5 eq. relative to compound (I).

E17. The process according to any of embodiments 14-16, wherein said N,N-diisopropylethylamine (DIPEA) is present in an amount of about 4.6 eq. relative to compound (I).

E18. A process for the preparation of compound (Id) from compound (I);
wherein said process comprises
step 2) according to any of embodiments 1 and 3-5; followed by
step 3) according to any of embodiments 8 and 10-11;
wherein compound A2 used in step 2) has been obtained by
step 1) according to any of embodiments 12-17.

E19. The compound (Id) with the formula below

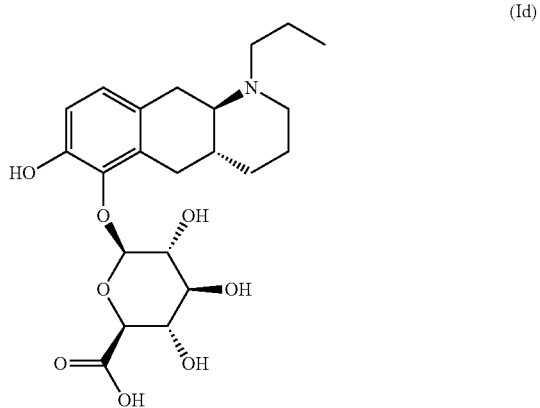 [SMILES: CCCN1CCC[C@@H]2Cc3c(ccc(O)c3O[C@@H]3O[C@H](C(=O)O)[C@@H](O)[C@H](O)[C@H]3O)C[C@H]21]

obtained by the process according to any of embodiments 1, 3-5 and 8-18.

E20. The process according to any one of embodiments 1, 3 to 5, 8, 10 to 11, and 12 to 17, wherein the process comprising an additional step of formulating compound Id into a solid oral dosage form.

Items

The following items serve to describe the invention and embodiments thereof.

Item 1. A process for the preparation of compound (Id) with the formula below, or a pharmaceutically acceptable salt thereof

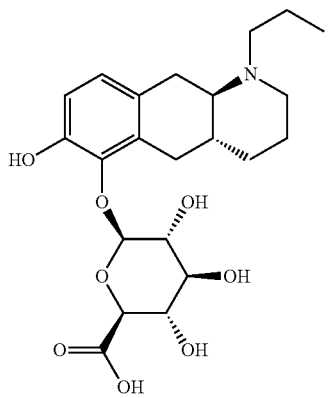

(Id)

from compound (I), with the formula below

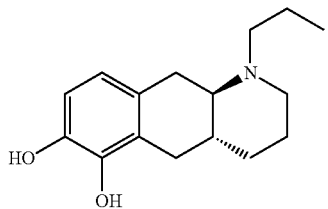

(I)

wherein said process comprises the following step
 2) reacting compound (A2) with (2S,3S,4S,5R,6R)-2-(methoxycarbonyl)-6-(2,2,2-trichloro-1-iminoethoxy)tetrahydro-2H-pyran-3,4,5-triyl triacetate to obtain compound (A3) according to the reaction scheme below

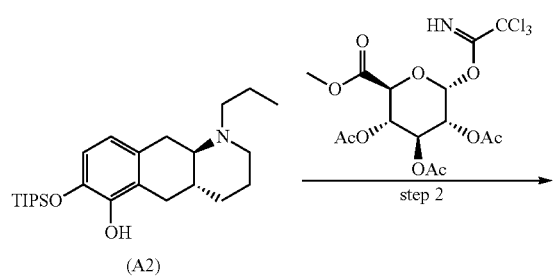

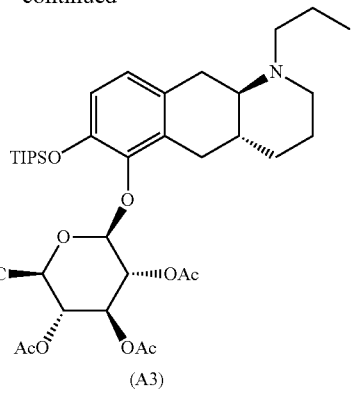

(A3)

wherein said reaction takes place in an aprotic solvent in the presence of a Lewis acid.

Item 2. A process for the manufacturing of compound (A3) below comprising the following step
 2) reacting compound (A2) with (2S,3S,4S,5R,6R)-2-(methoxycarbonyl)-6-(2,2,2-trichloro-1-iminoethoxy)tetrahydro-2H-pyran-3,4,5-triyl triacetate to obtain compound (A3) according to the reaction scheme below

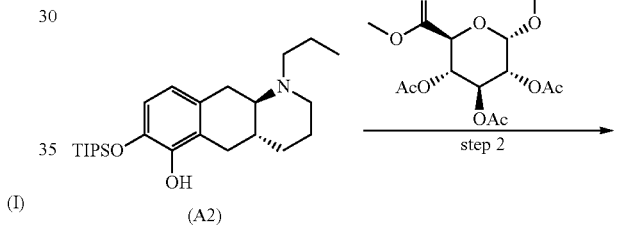

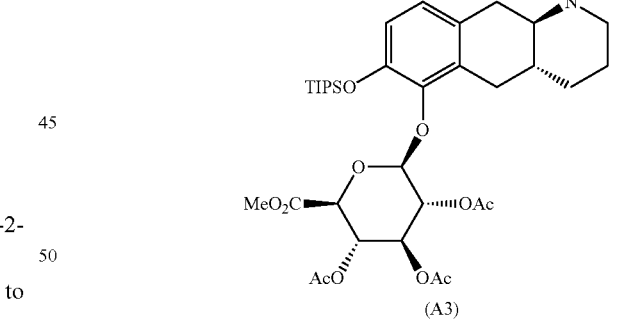

(A3)

wherein said reaction takes place in an aprotic solvent in the presence of a Lewis acid.

Item 3. The process according to any one of items 1-2, wherein step 2) comprises a step of isolating compound (A3).

Item 4. The process according to any one of items 1-3, wherein said aprotic solvent is dichloromethane or benzotrifluoride.

Item 5. The process according to any of items 1-4, wherein said aprotic solvent is dichloromethane and said Lewis acid is boron trifluoride diethyl etherate.

Item 6. The process according to any of items 1-4, wherein said aprotic solvent is benzotrifluoride and said Lewis acid is boron trifluoride diethyl etherate.

Item 7. A compound of formula (A3) below

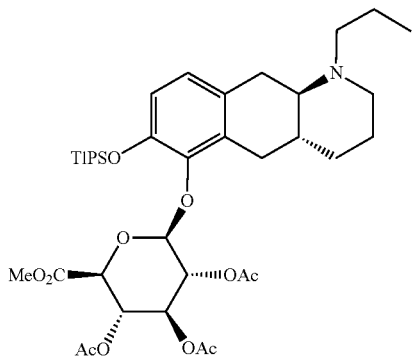

(A3)

or a salt thereof.

Item 8. Use of a compound according to item 7, in a process for the manufacture of the compound of formula (Id) or a pharmaceutically acceptable salt thereof.

Item 9. Compound (A3) directly obtained by the process according to any one of items 2-6.

Item 10. A process for the preparation of compound (Id) with the formula below

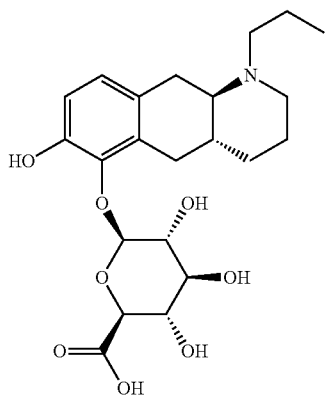

(Id)

or a pharmaceutically acceptable salt thereof, from compound (I) with the formula below

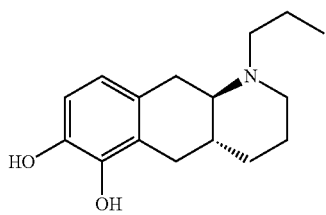

(I)

wherein said process comprises the following step
 3) deprotecting compound (A3) by contacting compound (A3) with a nucleophilic reagent to obtain compound (Id), or a pharmaceutically acceptable salt thereof according to the reaction scheme below

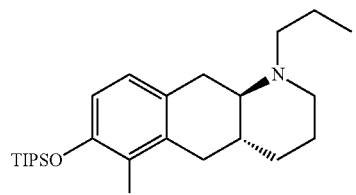

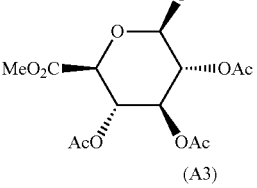

(A3)

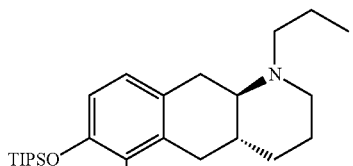

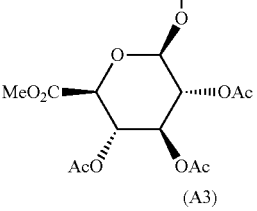

(Id)

Item 11. The process according to any one of items 1-6 wherein said process comprise a step 3) as defined below
 3) deprotecting compound (A3) by contacting compound (A3) with a nucleophilic reagent to obtain compound (Id), or a pharmaceutically acceptable salt thereof according to the reaction scheme below.

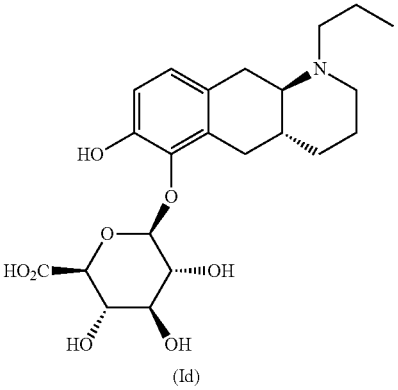

Item 12. The process according to any one of items 10-11, wherein said deprotection takes place in a mixture of methanol and water.

Item 13. The process according to any one of items 10-12, wherein said nucleophilic reagent used in step 3) is selected from potassium hydroxide, potassium cyanide, and sodium hydroxide.

Item 14. The process according to any one of items 10-13, wherein step 3) comprises the step of isolating compound (Id), or a pharmaceutically acceptable salt thereof.

Item 15. The process according to any one of items 13-14, wherein compound (Id) is obtained as a potassium salt of compound (Id), and wherein potassium hydroxide or potassium cyanide is used as nucleophilic reagent in step 3).

Item 16. The process according to any one of items 13-15, wherein compound (Id) is obtained as a potassium salt of compound (Id), and wherein potassium hydroxide is used as nucleophilic reagent in step 3).

Item 17. The process according to any one of items 10-14, wherein compound (Id) is obtained as a sodium salt of compound (Id), and wherein sodium hydroxide is used as nucleophilic reagent in step 3).

Item 18. The process according to any one of items 10-14, wherein a solution obtained in step 3) comprising compound (Id) is subsequently neutralized with a strong acid.

Item 19. The process according to item 18, wherein the strong acid is HCl.

Item 20. The process according to any one of items 18-19 wherein compound (Id) is obtained as (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid heptahydrate.

Item 21. The process according to any one of items 1-6 and 10-20, wherein compound (A2) has been obtained by the following step
 1) reacting compound (I), or a salt thereof with triisopropylsilyl chloride to obtain compound (A2) according to the reaction scheme below wherein the reaction takes place in an aprotic solvent in the presence of a base.

Item 22. The process according to item 21, wherein said aprotic solvent is dichloromethane, sulfolane or methyl-isobutylketone.

Item 23. The process according to any one of items 21-22, wherein said aprotic solvent is dichloromethane.

Item 24. The process according to any one of items 21-22, wherein said aprotic solvent is sulfolane.

Item 25. The process according to any one of items 21-22, wherein said aprotic solvent is methyl-isobutylketone.

Item 26. The process according to any one of items 21-25, wherein said base is N,N-diisopropylethylamine or triethylamine.

Item 27. The process according to item 21, wherein said aprotic solvent is dichloromethane and said base is N,N-diisopropylethylamine.

Item 28. The process according to any one of items 26-27, wherein said N,N-diisopropylethylamine (DIPEA) is present in an amount of 4-5 equivalents relative to the amount of compound (I).

Item 29. The process according to any one of items 21-28, wherein step 1) comprises a step of isolating compound (A2).

Item 30. A process for the preparation of compound (Id), or a pharmaceutically acceptable salt thereof, from compound (I);
 wherein said process comprises
  step 2) according to any one of items 1 and 3-6; followed by
  step 3) according to any one of items 11-20;
  wherein compound (A2) used in step 2) has been obtained by
  step 1) according to any one of items 21-29.

Item 30. The compound (Id) with the formula below or a pharmaceutically acceptable salt thereof
 obtained by the process according to any of items 1, 3-6, 11-20 and 21-29.

Item 31. The process according to any one of items 1 and 3-6, 11-20, 21-29, wherein the process comprises an additional step of formulating compound (Id), or pharmaceutically acceptable salt thereof into a solid oral dosage form.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", "such as" and "as such") in the present specification is intended merely to better illuminate the invention and does not pose a limitation on the scope of invention unless otherwise indicated.

It should be understood that the various aspects, embodiments, items, implementations and features of the invention mentioned herein may be claimed separately, or in any combination.

The present invention includes all modifications and equivalents of the subject-matter recited in the claims appended hereto, as permitted by applicable law.

Experimental Section

Preparation of the Compound of Formula (Id) and Intermediates

NMR Methods
QNMR (600 MHz):

| 1) Relaxation delay | 40 sec |
| 2) Acquisition time | 3.76 sec |
| 3) Time domain | 64k |
| 4) Size | 32k |
| 5) Dummy scans | 4 |
| 6) Scans | 8 |
| 7) Pulse | 30 deg |

LC-MS methods method A: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×150 mm operating at 60° C. with 0.6 ml/min of a binary gradient consisting of water+0.05% trifluoroacetic acid (A) and acetonitrile/water (95:5)+0.05% trifluoroacetic acid.

Gradient (linear):

| 0.00 min | 10% B |
| 3.00 min | 100% B |
| 3.60 min | 10% B |

Total run time: 3.6 minutes

Method B: LC-MS were run on Agilent 1260 HPLC consisting of column comp, Binary pump, Hip sample, and Single Q-MS equipped with ESI-source operating in positive ion mode.

LC-conditions: Column: Inertsustain AQ-C18 HP 3.0 μm; 3.0×50 mm operating at 35° C. with 1.2 ml/min of a binary gradient consisting of water+0.05% trifluoroacetic acid (A) and acetonitrile+0.05% trifluoroacetic acid (B).

Gradient (linear):

| 0.00 min | 0% B |
| 3.00 min | 95% B |
| 4.00 min | 95% B |

Total run time: 4.0 minutes

LC-MS Method C:
Instrument: Shimadzu LCMS-2020
Column: Phenomenex Kinetex EVO C18, 100×2.1 mm, 2.6 μm, ULC-016, UV-Vis Detector: 190-800 nm, Flow rate: 0.5 ml/min, Mobile Phase A: $H_2O$+0.1% HCOOH, Mobile Phase B: acetonitrile Gradient (linear):

| 1.00 min | 2% B |
| 10.00 min | 90% B |
| 13.00 min | 90% B |
| 13.10 min | 2% B |

Total run time: 13.1 minutes

Preparative HPLC method A:
Column: AQ gel, UV Detector: 210 nm, flow rate: 1 L/min, Mobile Phase A: Water (0.05% $NH_4HCO_3$), Mobile Phase B: acetonitrile.

Gradient (linear):

| 0.00 min | 5% B |
| 30.0 min | 30% B |

Total run time: 30.0 minutes

Preparative HPLC method B:
Column: RP-C18, 360 g column, Flow rate: 150 ml/min, UV Detector wavelength: 210 nm. Mobile Phase A: water, Mobile Phase B: acetonitrile Gradient (linear):

| 0.00 min | 5% B |
| 4.00 min | 30% B |

Total run time: 4.0 minutes

Quantitative HPLC:
Column: Phenomenex Synergi Polar RP, 150×4.6 mm×4.0 μm, Thermo-Dionex Ultimate 3000 Pump, Autosampler, Column compartment, Variable Wavelength Detector, Flow rate: 1 ml/min, UV Detector wavelength: 210 nm. Mobile Phase A: water-acetonitrile 98:2+0.1% trifluoroacetic acid, Mobile Phase B: acetonitrile+0.1% trifluoro-acetonitrile.

Gradient (linear):

| 0.00 min | 2% B |
| 6.00 min | 90% B |
| 9.00 min | 90% B |
| 9.50 min | 2% B |
| 15.0 min | 2% B |

Total run time: 15.0 minutes

Example 1: Preparation of Compound (A2)
(Step 1)

Example 1a

A 1 L three necked-flask was charged with 15 g (50.4 mmol, 1 eq.) HCl salt of compound (I), 450 ml dry dichloromethane, 40.4 ml (232 mmol) N,N-diisopropylethylamine (DIPEA) and 20.5 ml (96 mmol, 1.9 eq.) triisopropylsilyl chloride. The mixture was stirred at 20-25° C. under inert atmosphere. After 48 hours, the reaction mixture was cooled down to 0-5° C. and saturated NH$_4$Cl solution was added (300 ml). The mixture was stirred for 10 minutes and then the phases were separated. The organic layer was washed with deionized water (2×150 ml), dried on Na$_2$SO$_4$ and evaporated, affording compound (A2) (27.8 g). Used directly in the next step (example 2a).

LC-MS (method A): retention time (RT)=2.71 min, [M+H]$^+$=418.2 m/z.

Example 1b

Into a 3 L three-necked round-bottom flask purged and maintained with an inert atmosphere of nitrogen, was placed HCl salt of compound (I) (68 g, 228 mmol), dichloromethane (1.8 L), N,N-diisopropylethylamine (DIPEA) (83.6 g) and triisopropylsilyl chloride (135.7 g, 704.0 mmol). The resulting solution was stirred for 2 days at 25° C. The reaction was then quenched by the addition of 1000 mL of NH$_4$Cl. The resulting solution was extracted with dichloromethane (2×1 L) and the organic layers combined and concentrated under vacuum. The residue was purified using silica gel column chromatography (eluent: ethyl acetate/petroleum ether (1:1)). This afforded compound (A2) (78 g) as an oil. Used directly in the next step (example 2b).

LC-MS (method B): RT=1.606 min, [M+H]$^+$=418 m/z
$^1$H NMR (CDC$_3$, ppm): δ 6.64 (d, J=8.2 Hz, 1H), 6.49 (d, J=8.2 Hz, 1H), 3.11 (dd, J=15.5, 5.0 Hz, 1H), 2.97 (dd, J=17.5, 5.0 Hz, 1H), 2.80-2.50 (m, 3H), 2.23 (dd, J=17.5, 11.5 Hz, 1H), 1.95 (d, J=13.0 Hz, 1H), 1.80-1.65 (m, 3H), 1.41-1.23 (m, 3H), 1.16-1.03 (m, 33H, including TIPS impurity), 0.91 (t, J=7.5 Hz, 3H).

Example 2: Preparation of Compound (A3) (Step 2)

Example 2a

A 500 ml three-necked flask equipped with CaCl$_2$ tube was charged with compound (A2) (8.7 g, 21 mmol), anhydrous dichloromethane (260 mL) and (2S,3S,4S,5R,6R)-2-(methoxycarbonyl)-6-(2,2,2-trichloro-1-iminoethoxy)tetrahydro-2H-pyran-3,4,5-triyl triacetate (20 g, 42 mmol). The solution was cooled down to 0-5° C. and boron trifluoride diethyl etherate (5.2 mL, 42 mmol) was added dropwise. The reaction mixture was allowed to warm to room temperature and stirred overnight. The reaction mixture was poured into ice cold saturated solution of NaHCO$_3$ (770 mL). After 10 minutes stirring the phases were separated and the aqueous phase was extracted with dichloromethane (235 mL). The combined organic phase was dried on Na$_2$SO$_4$ and evaporated to dryness to give 27.9 g crude product as an oil.

The crude material was purified by normal phase silica gel column chromatography affording compound (A3) (first experiment: 7.2 g, >90% purity (Quantitative HPLC) (second experiment 2.2 g, ~80% purity (Quantitative HPLC).

LC-MS (method C): RT=8.33 min, [M+H]$^+$=418.4 m/z
$^1$H NMR: (CDCl$_3$, ppm): δ 6.98 (d, J=8.5 Hz, 1H), 6.84 (d, J=8.5 Hz, 1H), 5.38-5.30 (m, 3H), 5.12 (d, J=6.0 Hz, 1H), 4.26-4.17 (m, 1H), 3.77 (s, 3H), 3.18 (dd, J=16.0, 5.0 Hz, 1H), 3.10-2.96 (m, 2H), 2.86-2.70 (m, 1H), 2.31 (s, 3H), 2.15-2.00 (m, 10H), 1.91 (d, J=13.0 Hz, 1H), 1.55 (q, J=7.5 Hz, 2H), 1.35-1.20 (m, 3H), 1.16-1.04 (m, 1H), 1.01-0.90 (m, 24H).

Example 2b

Into a 3 L three-necked round-bottom flask purged and maintained with an inert atmosphere of nitrogen, was placed compound (A2) (60.0 g, 144 mmol, 1.0 eq), dichloromethane (1.2 L) and (2S,3S,4S,5R,6R)-2-(methoxycarbonyl)-6-(2,2,2-trichloro-1-iminoethoxy)tetrahydro-2H-pyran-3,4,5-triyl triacetate (351.3 g, 733.9 mmol). Then boron trifluoride diethyl etherate (150 g, 1.25 eq) was added dropwise at room temperature. The resulting solution was stirred for 2 days at 25° C. The reaction mixture was filtered and the filtrate was concentrated under vacuum. The residue was applied onto a silica gel column (eluent: ethyl acetate/petroleum ether (1:10)) affording compound (A3) (75 g) of as a solid.

LC-MS (method B): RT=3.531 min. [M+H]$^+$=720 m/z
$^1$H NMR: (CDCl$_3$, ppm): δ 6.98 (d, J=8.5 Hz, 1H), 6.84 (d, J=8.5 Hz, 1H), 5.38-5.30 (m, 3H), 5.12 (d, J=6.0 Hz, 1H), 4.26-4.17 (m, 1H), 3.77 (s, 3H), 3.18 (dd, J=16.0, 5.0 Hz, 1H), 3.10-2.96 (m, 2H), 2.86-2.70 (m, 1H), 2.31 (s, 3H), 2.15-2.00 (m, 10H), 1.91 (d, J=13.0 Hz, 1H), 1.55 (q, J=7.5 Hz, 2H), 1.35-1.20 (m, 3H), 1.16-1.04 (m, 1H), 1.01-0.90 (m, 24H).

Example 3: Preparation of Compound (Id) (Step 3)

Example 3a (Using KOH)

Into a 10 L three-necked round-bottom flask purged and maintained with an inert atmosphere of nitrogen, was placed compound (A3) (75 g, 102 mmol), methanol (4 L), and water (375 mL). This was followed by the addition of potassium hydroxide (28.7 g), NH$_4$F (3.8 g) at 0° C. The resulting solution was stirred overnight at 25° C. The resulting solution was neutralized with 1 N HCl (~200 mL, pH adjusted to 7.1) and concentrated under reduced pressure to afford a 250 mL solution. The solution was purified by preparative HPLC (method A) affording compound (Id) (40 g) as a solid. The afforded compound (Id) is obtained as a heptahydrate of compound (Id).

LC-MS (method B): RT=1.902 min, [M+H]$^+$=438.3 m/z.
$^1$H NMR (300 MHz, D$_2$O): δ 6.83 (d, J=8.5 Hz, 1H), 6.74 (d, J=8.5 Hz, 1H), 4.74 (d, J=7.5 Hz, 1H), 3.59-3.54 (m, 2H), 3.54-3.45 (m, 3H) 3.36-3.13 (m, 4H), 3.08-2.99 (m, 2H), 2.72 (dd, J=14.5, 12.0 Hz, 1H), 2.27 (dd, J=17.5, 11.5 Hz, 1H), 1.95 (t, J=15.0 Hz, 2H), 1.88-1.68 (m, 3H), 1.68-1.58 (m, 1H), 1.31 (dq, J=13.5, 3.5 Hz, 1H), 0.91 (t, J=7.5 Hz, 3H).

Example 3b (Comparative Example Using KCN)

In a three-necked flask 6.1 g (8.2 mmol) compound (A3) was dissolved in 260 ml MeOH/water (12:1) mixture and treated with 10.0 g KCN (19 eq.) at 0° C. After addition, the reaction mixture was stirred at room temperature. After 16 hours the reaction mixture was filtered to remove the insoluble inorganic salts. The filtrate was evaporated to dryness to give 15.2 g crude compound (Id). The crude product was purified by preparative HPLC (method B) affording compound (Id) (2.8 g) as a solid. The afforded compound (Id) is obtained as a potassium salt of compound (Id).

LC-MS (method C): RT=4.17 min, [M+H]$^+$=438.3 m/z.
In vitro and in vivo characterization of compound (Id)

Example 4a: Conversion of the Compound of Formula (Id) in Rat and Human Hepatocytes Compound (Id) was incubated at 1 μg/mL with hepatocytes from human or rat suspended in DMEM (Dulbecco's Modified Eagle Medium) with HEPES (4-(2-hydroxyethyl)-1-piperazineethanesulfonic acid) at pH 7.4. The cell concentration at incubation was 1×10$^6$ viable cells/mL. The incubations were performed in glass tubes at 37° C. with a total incubation volume of 3.5 mL and with duplicate incubations for each test item. The 3.5 mL of hepatocyte suspension was equilibrated for 10 minutes in a water bath set to 37° C. where after the incubations were initiated by adding 3.5 µL of a stock solution of the test item in DMSO (Dimethyl sulfoxide) and gently inverting the tubes. The final solvent concentration in the incubations was 0.1% DMSO. Samples of 600 µL were withdrawn from the incubations at the pre-determined time points of 0.25, 5, 15, 30 and 60 minutes after ensuring homogeneity of hepatocyte suspensions. The withdrawn volume was added to 1 mL Nunc cryotubes on wet ice containing 60 µL of ice-cold ascorbic acid (100 mg/mL) and 30 µL of ice cold 100 mM saccharic acid 1.4-lactone in 0.5 M citric acid. The tubes were mixed and 35 µL of a solution of ice cold 20% formic acid was added. The tubes were mixed thoroughly and stored at −80° C. awaiting analysis. Analysis method and Instrumentation used for analysis of (I) from dosing compound (Id) was the one described in Example 7 below in the section "Instrumentation used for analysis of compound (I) from dosing of compound (Ic) and (Id)."

FIG. 6 indicates a time dependent conversion to compound (I) from (Id) in both rat and human hepatocytes.

Example 4b: Conversion of the Compound of Formula (Id) in Fresh Rat and Human Blood Conversion of (Id) in human blood (average of 3 donors) and rat blood (average of 45 donors) to (I) was shown in fresh blood at 37° C. spiked with 1 µg/mL of (Id). (I) was measured at 0, 5, 15, 30 and 60 minutes in isolated plasma. Analysis method and Instrumentation as described in Example 7 below in the section "Instrumentation used for analysis of compound (I) from dosing of compounds (Ic) and (Id)."

FIG. 7 indicates a time dependent conversion to compound (I) from (Id), in both rat and human blood.

Example 5: Dopamine Agonist Activity

Dopamine D1 Receptor Agonism

Dopamine D1 receptor agonism was measured using a HTRF cAMP from CisBio using the protocol developed by HD Biosciences (China). Briefly, the assay is a homogeneous time resolved-fluorescence resonance energy transfer (HTRF) assay that measures production of cAMP by cells in a competitive immunoassay between native cAMP produced by cells and cAMP-labeled with XL-665. A cryptate-labeled anti-cAMP antibody visualizes the tracer. The assay was performed in accordance with instructions from manufacturer.

Test compounds were added to wells of microplates (384 format). HEK-293 cells expressing the human D1 receptor were plated at 1000 cells/well and incubated 30 minutes at room temperature. cAMP-d2 tracer was added to wells and followed by addition of Anti-cAMP antibody-cryptate preparation and incubated for 1 hour at room temperature in dark. HTRF cAMP was measured by excitation of the donor with 337 nm laser (the "TRF light unit") and subsequent (delay time 100 microseconds) measurement of cryptate and d2 emission at 615 nm and 665 nm over a time window of 200 microseconds with a 2000 microseconds time window between repeats/100 flashes). HTRF measurements were performed on an Envision microplate reader (PerkinElmer). The HTRF signal was calculated as the emission-ratio at 665 nm over 615 nm. The HTRF ratio readout for test compounds was normalized to 0% and 100% stimulation using control wells with DMSO-solvent or 30 µM dopamine. Test compound potency (EC$_{50}$) was estimated by nonlinear regression using the sigmoidal dose-response (variable slope) using Xlfit 4 (IDBS, Guildford, Surrey, UK, model 205).

$$y=(A+((B-A)/(1+((C/x)^D))))$$

where y is the normalized HTRF ratio measurement for a given concentration of test compound, x is the concentration of test compound, A is the estimated efficacy at infinite compound dilution, and B is the maximal efficacy. C is the EC$_{50}$ value and D is the Hill slope coefficient. EC$_{50}$ estimates were obtained from an independent experiment and the logarithmic average was calculated.

Dopamine D2 Receptor Agonism

Dopamine D2 receptor agonism was measured using a calcium mobilization assay protocol developed by HD Biosciences (China). Briefly, HEK293/G15 cells expressing human D2 receptor were plated at a density of 15000 cells/well in clear-bottomed, Matrigel-coated 384-well plates and grown for 24 hours at 37° C. in the presence of 5% CO$_2$. The cells were incubated with calcium-sensitive fluorescent dye, Fluo8, for 60-90 minutes at 37° C. in the dark. Test compounds were prepared at 3-fold concentrated solution in 1×HBSS buffer with Ca$^{2+}$ and Mg$^{2+}$. Calcium Flux signal was immediately recorded after compounds were added from compound plate to cell plate at FLIPR (Molecular Devices). The fluorescence data were normalized to yield responses for no stimulation (buffer) and full stimulation (1 µM of dopamine) of 0% and 100% stimulation, respectively. Test compound potency (EC$_{50}$) was estimated by nonlinear regression using the sigmoidal dose-response (variable slope) using Xlfit 4 (IDBS, Guildford, Surrey, UK, model 205).

$$y=(A+((B-A)/(1+((C/x)^D))))$$

where y is the normalized ratio measurement for a given concentration of test compound, x is the concentration of test compound, A is the estimated efficacy at infinite compound dilution, and B is the maximal efficacy. C is the EC$_{50}$ value and D is the Hill slope coefficient. EC$_{50}$ estimates were obtained from independent experiment and the logarithmic average was calculated.

Example 6: 5-HT2B Agonist Activity and Binding Assay

5-HT2B Agonist Activity Assay

Evaluation of the agonist activity of compounds (I), (Ia), (Ib), (Ic) and (Id) at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM CaCl$_2$, 0.5 mM MgCl$_2$, 5.5 mM glucose and 50 mM LiCl, then distributed in microplates at a density of 4100 cells/well and incubated for 30 minutes at 37° C. in the presence of buffer (basal control), test compound or reference agonist. For stimulated control measurement, separate assay wells contained 1 µM 5-HT. Following incubation, the cells were lysed and the fluorescence acceptor (fluorophen D2-labeled IP1) and fluorescence donor (anti-IP1 antibody labeled with europium cryptate) were added. After 60 minutes at room temperature, the fluorescence transfer was measured at lambda (Ex) 337 nm and lambda (Em) 620 and 665 nm using a microplate reader (Rubystar, BMG). The IP1 concentration was determined by dividing the signal measured at 665 nm by that measured at 620 nm (ratio). The results were expressed as a percent of the control response to 1 µM 5-HT. The standard reference agonist was 5-HT, which was tested in each experiment at several concentrations to generate a concentration-response curve from which its $EC_{50}$ value is calculated as described above for dopamine functional assays.

5-HT2B Binding Assay

Evaluation of the affinity of compound (Id) for the human 5-HT2B receptor was determined in a radioligand binding assay at Eurofins/Cerep (France). Membrane homogenates prepared from CHO cells expressing the human 5HT2B receptor were incubated for 60 minutes at room temperature with 0.2 nM [125I](±)DOI (1-(4-iodo-2, 5-dimethoxyphenyl)propan-2-amine) in the absence or presence of the test compound in a buffer containing 50 mM Tris-HCl (pH 7.4), 5 mM $MgCl_2$, 10 µM pargyline and 0.1% ascorbic acid. Nonspecific binding is determined in the presence of 1 µM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 2

In vitro activities for the compounds of formula (I), (Ia), (Ib), (Ic) and (Id) obtained according to Examples 5 and 6

| | Compound | D1 $EC_{50}$ (nM)/$E_{max}$ | D2 $EC_{50}$ (nM)/$E_{max}$ | 5-HT2B $EC_{50}$ (nM)/$E_{max}$ |
|---|---|---|---|---|
| Parent compound | (I) | 3.3/99% | 1.3/91% | 2900 nM/50% |
| Prodrugs in the state of the art | (Ia) | >1000 | >1000 | >6000 nM, 58% @ 30 µM |
| | (Ib) | >1000 | 46 nM/100% | 3.8 nM/79% |
| | (Ic) | nd | nd | −5% @ 10 µM |
| Compound obtained by the invention | (Id) | 2700/98% | 1100/92% | −25% @ 10 µM* |

*indicate binding affinity (% inhibition of control, specific binding at concentration indicated)
nd: not determined Example 7: PK Experiments in Rats For all the experiments, blood samples of approximately 0.68 mL were drawn from the tail or sublingual vein and put into $K_3$EDTA tubes that had been pre-cooled and prepared with stabilizing solution consisting of 80 µL ascorbic acid and 40 µL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 µL plasma were transferred to each of three appropriately labelled cryotubes containing 6.5 µL pre-cooled formic acid (20%) (the tubes were pre-spiked and stored refrigerated prior to use). The tube lid was immediately replaced and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters.

Instrumentation Used for Analysis of Compound (I) from Dosing Compound (Ia):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 min. Flow rate 0.5 mL/min. MRM monitoring (multiple reaction monitoring) of test item and the added analytical standards Dosing and blood sampling: Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 µg/kg (Ia), blood samples from 3 male satellite animals were collected on the following time points at Day 29: 0.5, 1, 2, 4, 6, 8, 12 and 24 hours after dosing.

Instrumentation Used for Analysis of Compound (I) from Dosing of Compound (Ib):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 min. Flow rate 0.5 mL/min. MRM monitoring of test item and the added analytical standards.

Dosing and blood sampling: Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 µg/kg (Ib), blood samples from 3 male satellite animals were collected on the following time points at day 182: 0.5, 1, 2, 4, 8 and 24 hours after dosing.

Instrumentation used for analysis of compound (I) from dosing of compounds (Ic) and (Id): Mass spectrometer (LC-MS/MS) Waters Acquity-Waters Xevo TQ-S. Analytical column Acquity BEH C18 100×2.1 mm, 1.7 µm. Mobile phase A: 20 mM $NH_4$—Formate+0.2% formic acid. Mobile phase B: Acetonitrile+0.2% formic acid. Gradient run from 95/5% to 5/95% in 11.0 min. Flow rate 0.3 mL/min. MRM monitoring of test item and the added analytical standards.

Dosing and blood sampling for compound (Id): Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet. Male Han Wistar rats were dosed a single oral gavage administration of compound (Id) orally by gavage. Rats were given 633 µg/kg of compound (Id), blood samples from 3 male animals were collected on the following time points at Day 1: 1, 2, 4, 6, 8, and 24 hours after dosing.

Dosing and blood sampling for compound (Ic): Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of (Ic). Rats were given 494 µg/kg (Ic). Blood samples from 3 male animals were collected on the following time points at Day 1: 1, 2, 4, 6, 8, and 24 hours after dosing Instrumentation used for analysis of apomorphine: Mass spectrometer (UPCLC-MS/MS) Waters Acquity I-Class-Waters Xevo TQ-S. Analytical column Acquity HSS T3 C18 50×2.1 mm, 1.8 µm. Mobile phase A: 10 mM $NH_4$—Formate 0.2% formic acid:acetonitril (95:5). Mobile phase B: 10 mM $NH_4$—Formate 0.2% formic acid:acetonitril (5:95). Gradient run from 95/5% to 5/95% in 2.40 minutes. Flow rate 0.3 mL/min. MRM detection of test items and the added analytical standards.

Dosing and blood sampling for Apomorphine: Animals for the study were as described in Dosing and blood sampling for compound (Id). Additionally, rats were administered a single dose of apomorphine subcutaneously. From rats administered 3000 µg/kg (apomorphine), blood samples from 3 male animals were collected on the following time points at Day 1: 0.25, 0.5, 1, 1.5, 2, 3, 5 and 7 hours SC administration after dosing.

to food and water. The experiment described below was performed in accordance with the standard operating procedures of Charles River Discovery Research Services Finland Ltd. and in accordance with the national Animal Experiment Board of Finland (Eläinkoelautakunta, ELLA) authority on animal testing.

Locomotor Activity Testing, Open Field

The test device is a square Plexiglass-arena (measuring 40×40×40 cm), in which the movement paths of the rats are recorded by an activity monitor (Med. Associates Inc.). Before the test period is initiated, rats are habituated to their test cage for 60 minutes. Upon completion of habituation, animals were treated with either compound or vehicle and placed back into the open field apparatus. The main test parameter measured is ambulatory distance (recorded in 5-minute segments). Overall time of measurement after receiving initial treatment was 360 minutes. Total follow up period in the study was 420 min, including 60 min of habituation.

Results

Oral administration of compound (Id) was assessed in the rat locomotor activity assay, and this functional readout was then correlated to plasma concentrations of compound (I). Apomorphine and pramipexole were also concomitantly tested in this assay as comparators (i.e. known standard-of-care (SoC) in the Parkinson's Disease field), and plasma concentration was analyzed for apomorphine.

As shown in FIG. 2, compound (Id) (10 to 300 µg/kg, p.o.) increases locomotor activity with an effect starting approximately 2 hours post-administration (around the 180-minute time point) and lasting until the end of recording (at the 415-minute time point). In contrary, the hyperactivity induced by apomorphine (3 mg/kg, s.c.) is immediate but short-lasting as the effect is gone 1.5 hours. post administration (at the 150-minute time point). Pramipexole (0.3 mg/kg, s.c.) also induces an increase in activity, but its effect appears about 1 hour post administration and is gone 2.5 hours later (at the 270-minute time point). The total distance travelled as seen in FIG. 3 demonstrates a significantly increased activity for both compound (Id) and the two

TABLE 3

PK parameters for (4aR,10aR)-1-Propyl--1,2,3,4,4a,5,10,10a-octahydro-benzo[g]quinoline-6,7-diol (compound (I)) after oral dosing of 0.300 mg/kg (Ia), 0.300 mg/kg (Ib), 0.633 mg/kg of TFA salt of compound (Id) and 494 µg/kg (Ic) to Wistar rats according to Example 7

|  | compound | $T_{max}$ (hour) | $C_{max}$ (pg/mL) | $AUC_{0-24}$ (pg * h/mL) | $t_{1/2}$ (hour) | Exposure at 24 h (pg/mL) |
|---|---|---|---|---|---|---|
| Prodrugs in the state of the art | (Ia) | 1.0 | 3160 | 13600 | 4.09 | 48 ± 26 |
|  | (Ib) | 0.5 | 4990 | 31000 | N/A | 147 ± 28 |
|  | (Ic) | 1.0 | 14 | 104 | N/A | N/A |
| Compound obtained by the invention | (Id) | 4.0 | 1350 | 15500 | 6.8 | 208 ± 89 |

Example 8: PK/PD of Compound (Id)/Compound (I) in Rat Hyperactivity Assay

Animals

In total, 206 male CD rats (Charles River, Germany) weighing 200-250 grams (165-190 grams upon arrival) were used in the study. Animals were housed at a standard temperature (22±1° C.) and in a light-controlled environment (lights on from 7 am to 8 µm) with ad libitum access comparators tested, and this effect is the one that is to be expected from dopamine agonists.

In parallel with the locomotor activity assessment, plasma samples were taken from satellite animals at 6 different time points (1.5, 2, 3, 4, 5 & 7 hours post-dose for animals treated with compound (Id)). Pharmacokinetic analysis demonstrates that the behavioural effects of compound (Id) (100 µg/kg, p.o.) correlate with the plasma concentrations of compound (I) (see FIG. 4), demonstrating that the behavioural effect of compound (Id) is driven by Compound (I) rather than by Compound (Id) itself. The corresponding exposure analysis of apomorphine (at 1.25, 1.5, 2, 3, 5 & 7 hours post-dose) resulted in a correlation between plasma concentrations of apomorphine and hyperactive behaviour (see FIG. 5).

REFERENCE LIST

U.S. Pat. No. 4,543,256
WO2001/078713
WO 02/100377
WO2009/026934
WO2009/026935
WO2010/097092
WO2019101917
Alexander et Crutcher, (1990) Trends in Neuroscience 13: 266-71;
Bibbiani et al., Chase Experimental Neurology (2005), 192: 73-78;
Campbell et al., Neuropharmacology (1982); 21(10): 953-961;
Cannon et al., J. Heterocyclic Chem. (1980); 17: 1633-1636;
Cavero and Guillon, J. Pharmacol. Toxicol. Methods (2014), 69: 150-161;
Delong, (1990) Trends in Neuroscience 13: 281-5;
Gerfen et al, Science (1990) 250: 1429-32;
Giardina and Williams; CNS Drug Reviews (2001), Vol. 7 (3): 305-316;
Goswami et al., J. Nutritional Biochem. (2003) 14: 703-709;
Grosset et al., Acta Neurol Scand. (2013), 128:166-171;
Hauser et al., Movement Disorders (2016), Vol. 32 (9): 1367-1372;
Liu et al., J. Med. Chem. (2006), 49: 1494-1498;
Liu et al., Bioorganic Med. Chem. (2008), 16: 3438-3444;
Nolen et al., J. Pharm Sci. (1995), 84 (6): 677-681;
Poewe et al., Nature Review, (2017) vol 3 article 17013: 1-21;
Remington, "The Science and Practice of Pharmacy", 22$^{th}$ edition (2013), Edited by Allen, Loyd V., Jr.
Rothman et al., Circulation (2000), 102: 2836-2841;
Sprenger and Poewe, CNS Drugs (2013), 27: 259-272;
Sozio et al., Exp. Opin. Drug Disc. (2012); 7(5): 385-406;
Stain-Texier et al., Drug Metab. and Disposition (1998) 26 (5): 383-387;
Wiley-Interscience (publisher): Compendium of Organic Synthetic Methods, Vol. I-XII

The invention claimed is:

1. A process for the preparation of compound (Id)

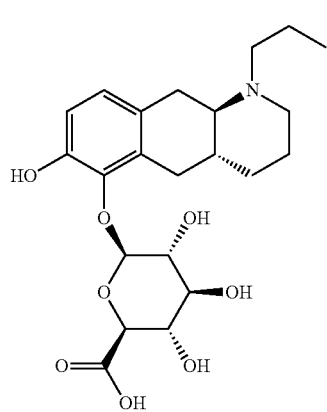

(Id)

or a pharmaceutically acceptable salt thereof, comprising deprotecting compound (A3) to obtain compound (Id), or a pharmaceutically acceptable salt thereof, according to the reaction scheme below:

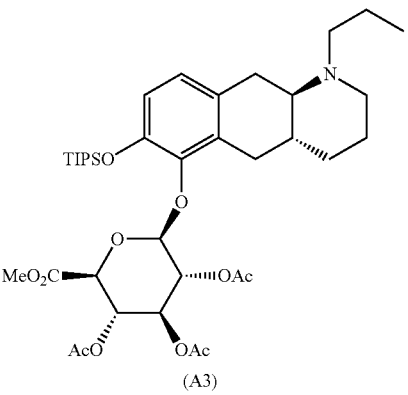

(A3)

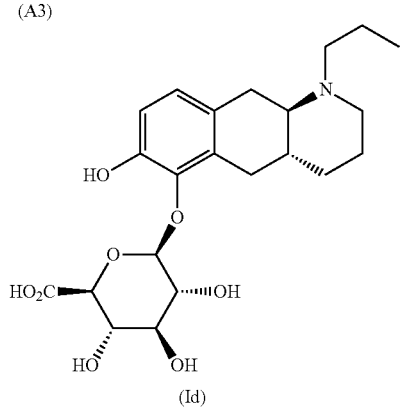

(Id)

2. The process of claim 1, comprising deprotecting compound (A3) by contacting compound (A3) with a nucleophilic reagent to obtain compound (Id), or a pharmaceutically acceptable salt thereof.

3. The process according to claim 2, further comprising the step of isolating compound (Id), or a pharmaceutically acceptable salt thereof.

4. The process according to claim 2, wherein said nucleophilic reagent is selected from potassium hydroxide, potassium cyanide, and sodium hydroxide.

5. The process according to claim 2, wherein said deprotection takes place in a mixture of methanol and water.

6. The process according to claim 2, wherein compound (Id) is obtained as a potassium salt of compound (Id), and wherein potassium hydroxide or potassium cyanide is used as nucleophilic reagent.

7. The process according to claim 2, wherein compound (Id) is obtained as a potassium salt of compound (Id), and wherein potassium hydroxide is used as nucleophilic reagent.

8. The process according to claim 2, wherein compound (Id) is obtained as a sodium salt of compound (Id), and wherein sodium hydroxide is used as nucleophilic reagent.

9. The process according to claim 4, wherein compound (Id) is obtained in a solution, and the process further comprises neutralizing the solution with a strong acid.

10. The process according to claim 9, wherein the strong acid is HCl.

11. The process according to claim 2, wherein compound (Id) is obtained as (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid heptahydrate.

12. The process according to claim 6, further comprising formulating the potassium salt of compound (Id) into a solid oral dosage form.

13. The process according to claim 7, further comprising formulating the potassium salt of compound (Id) into a solid oral dosage form.

14. The process according to claim 8, further comprising formulating the sodium salt of compound (Id) into a solid oral dosage form.

15. The process according to claim 9, further comprising formulating compound (Id), or a pharmaceutically acceptable salt thereof, into a solid oral dosage form.

16. The process according to claim 11, further comprising formulating (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid heptahydrate compound (Id) into a solid oral dosage form.

17. The process according to claim 2, wherein compound (A3) is prepared using the following step reacting compound (A2) with (2S,3S,4S,5R,6R)-2-(methoxycarbonyl)-6-(2,2,2-trichloro-1-iminoethoxy)tetrahydro-2H-pyran-3,4,5-triyl triacetate to obtain compound (A3) according to the reaction scheme below

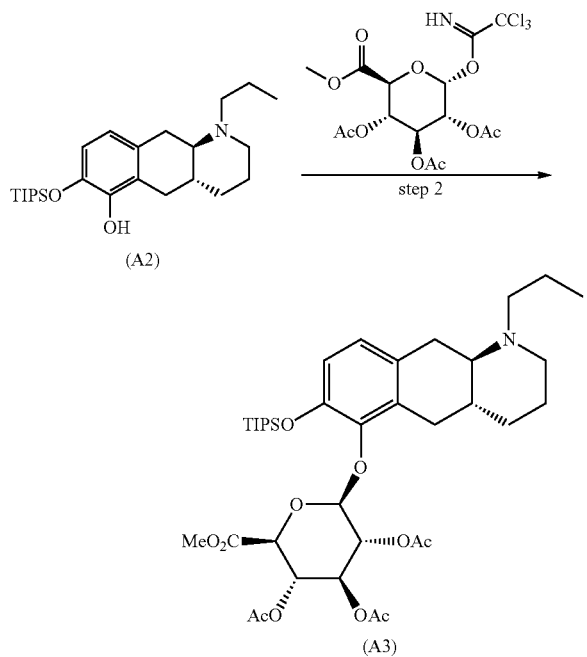

wherein said reaction takes place in an aprotic solvent in the presence of a Lewis acid.

18. The process according to claim 17, further comprising the step of isolating compound (A3).

19. The process according to claim 17, wherein said aprotic solvent is dichloromethane or benzotrifluoride.

20. Previously presented 17, The process according to claim 17, wherein said aprotic solvent is dichloromethane, and said Lewis acid is boron trifluoride diethyl etherate.

21. The process according to claim 17, wherein said aprotic solvent is benzotrifluoride, and said Lewis acid is boron trifluoride diethyl etherate.

* * * * *

UNITED STATES PATENT AND TRADEMARK OFFICE
CERTIFICATE OF CORRECTION

PATENT NO. : 11,827,665 B2
APPLICATION NO. : 17/385166
DATED : November 28, 2023
INVENTOR(S) : Martin Juhl et al.

It is certified that error appears in the above-identified patent and that said Letters Patent is hereby corrected as shown below:

In the Claims

Column 44, Claim 20, the text:
20. Previously presented 17, The process according to claim 17, wherein said aprotic solvent is dichloromethane, and said Lewis acid is boron trifluoride diethyl etherate.
Should read:
20. The process according to claim 17, wherein said aprotic solvent is dichloromethane, and said Lewis acid is boron trifluoride diethyl etherate.

Signed and Sealed this
Twenty-sixth Day of December, 2023

Katherine Kelly Vidal
*Director of the United States Patent and Trademark Office*